(12) United States Patent
Sayles

(10) Patent No.: US 9,370,401 B2
(45) Date of Patent: Jun. 21, 2016

(54) MILLIMETER-SIZED RECOGNITION SIGNAL BADGE AND IDENTIFICATION SYSTEM FOR ACCURATELY DISCERNING AND SORTING AMONG SIMILAR KINDS, SHAPES, AND SIZES OF SURGICAL INSTRUMENTS

(71) Applicant: Philip W. Sayles, Newburyport, MA (US)

(72) Inventor: Philip W. Sayles, Newburyport, MA (US)

( * ) Notice: Subject to any disclaimer, the term of this patent is extended or adjusted under 35 U.S.C. 154(b) by 12 days.

(21) Appl. No.: 14/120,246

(22) Filed: May 12, 2014

(65) Prior Publication Data

US 2015/0320506 A1 Nov. 12, 2015

(51) Int. Cl.
*G06F 19/00* (2011.01)
*A61B 19/00* (2006.01)
*G06K 19/077* (2006.01)
*G06K 7/10* (2006.01)
*G06K 19/073* (2006.01)
*G06K 19/07* (2006.01)
*G06K 17/00* (2006.01)

(52) U.S. Cl.
CPC .............. *A61B 19/44* (2013.01); *G06K 7/1097* (2013.01); *G06K 19/0723* (2013.01); *G06K 19/07345* (2013.01); *G06K 19/07758* (2013.01); *G06K 2017/0045* (2013.01)

(58) Field of Classification Search
CPC ............. G06K 19/0723; G06K 19/07345; G06K 19/0707; G06K 19/07758; G06K 7/1097; G06K 2017/0045; G06Q 10/087; H04Q 2209/47
USPC ....................................................... 235/385
See application file for complete search history.

(56) References Cited

U.S. PATENT DOCUMENTS

| 6,335,685 | B1* | 1/2002 | Schrott | G06K 7/10079 235/385 |
|---|---|---|---|---|
| 8,600,374 | B1* | 12/2013 | Hertlein | H04M 1/18 455/425 |
| 2001/0014377 | A1* | 8/2001 | Babb | B60C 23/0493 428/40.1 |
| 2002/0036237 | A1* | 3/2002 | Atherton | G06K 19/073 235/492 |
| 2002/0067263 | A1* | 6/2002 | Tafoya | G06K 17/00 340/572.1 |
| 2003/0062988 | A1* | 4/2003 | Mandecki | G06K 7/1097 340/10.1 |
| 2004/0246099 | A1* | 12/2004 | Tuttle | G01S 13/758 340/10.1 |
| 2006/0119481 | A1* | 6/2006 | Tethrake | A61B 19/0248 340/572.1 |
| 2006/0290498 | A1* | 12/2006 | Rawlings | G06K 19/07749 340/572.1 |
| 2008/0042839 | A1* | 2/2008 | Grater | G01N 35/00732 340/572.1 |

(Continued)

FOREIGN PATENT DOCUMENTS

GB 2410151 A * 7/2005 ......... G06K 19/0704

*Primary Examiner* — Thien M Le
*Assistant Examiner* — Claude J Brown
(74) *Attorney, Agent, or Firm* — David Prashker, Esq.

(57) ABSTRACT

The present invention is a discrete signal-identifying badge and operative system for recognizing, differentiating and distinguishing among the many kinds, shapes and sizes of surgical instruments and tools commonly used today for human and veterinary surgeries and in scientific research. The signal-identifying badge is a discrete millimeter-sized article of manufacture which can be easily affixed to an exposed surface of any type, any configuration and any dimension of surgical instrument or tool; and includes a well-cushioned and protected photovoltaic cell-integrated chip transponder unit embedded within a safeguarding three-tier stack construct.

11 Claims, 20 Drawing Sheets

(56) References Cited

U.S. PATENT DOCUMENTS

| | | | | |
|---|---|---|---|---|
| 2008/0094201 A1* | 4/2008 | Paradiso | G06K 19/0723 | 340/505 |
| 2008/0174436 A1* | 7/2008 | Landt | G06K 19/07749 | 340/572.7 |
| 2008/0180242 A1* | 7/2008 | Cottingham | G06K 19/0723 | 340/539.12 |
| 2008/0180255 A1* | 7/2008 | Isabell | G06K 19/07749 | 340/572.8 |
| 2009/0237223 A1* | 9/2009 | Zimmerman | G06K 19/0707 | 340/10.51 |
| 2010/0060421 A1* | 3/2010 | Chang | H01Q 1/2208 | 340/10.1 |
| 2010/0093429 A1* | 4/2010 | Mattice | G07F 1/06 | 463/25 |
| 2010/0156640 A1* | 6/2010 | Forster | G06K 7/0008 | 340/572.1 |
| 2010/0316841 A1* | 12/2010 | Geuens | B32B 37/185 | 428/137 |
| 2011/0068177 A1* | 3/2011 | Harris | G06K 19/00 | 235/492 |
| 2011/0114732 A1* | 5/2011 | Reignoux | G06K 19/025 | 235/488 |
| 2011/0169657 A1* | 7/2011 | August | A01K 11/004 | 340/854.6 |
| 2012/0000985 A1* | 1/2012 | Bove | G06K 19/07345 | 235/492 |
| 2012/0056002 A1* | 3/2012 | Ritamaki | G06K 19/07786 | 235/492 |
| 2012/0126008 A1* | 5/2012 | Binmore | G06K 19/0723 | 235/439 |
| 2013/0212694 A1* | 8/2013 | Castiglia | G06F 21/60 | 726/26 |
| 2014/0239074 A1* | 8/2014 | Wang | G06K 19/07749 | 235/488 |
| 2015/0061833 A1* | 3/2015 | Do | G06K 19/07715 | 340/6.11 |
| 2015/0272690 A1* | 10/2015 | Deng | A61B 17/28 | 606/174 |
| 2016/0042130 A1* | 2/2016 | Broninx | A61B 19/44 | 705/2 |

* cited by examiner

Prior Art Fig. 1
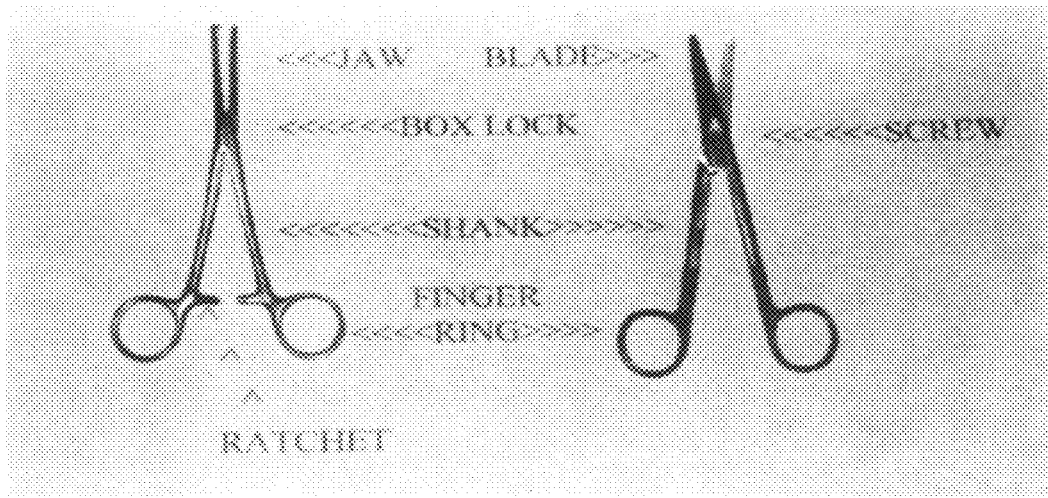
Prior Art Fig. 2
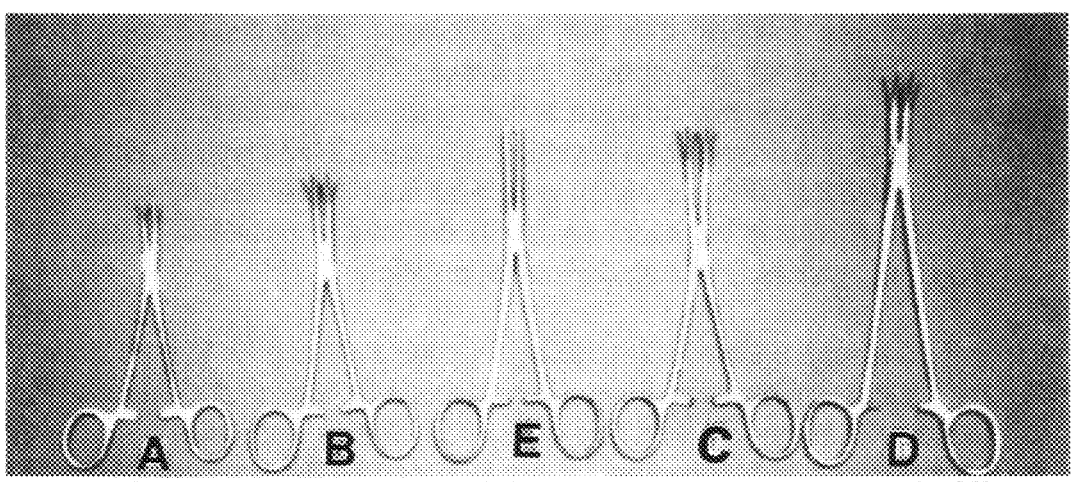
Hemostatic Forceps: (A) Mosquite, (B) Kelly, (C) Kocher, (D) Carmalt, (E) Schnidt Tonsil

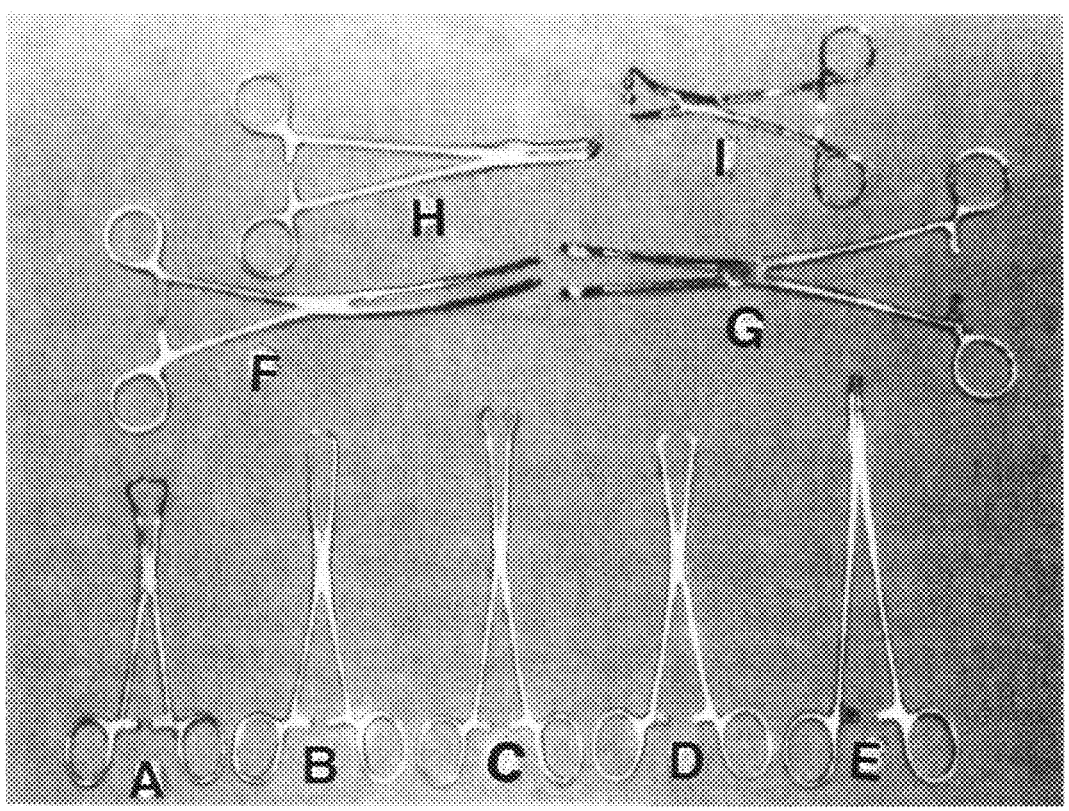
Prior Art Fig. 3
Soft Tissue Forceps: (A) Backhaus Towel, (B) Allis Intestinal, (C) Babcock Intestinal, (D) Lahey Goiter, (E) Mixter Gall Duct, (F) Doyen Intestinal, (G) Forrester Sponge, (H) Kantorwitz Right Angle

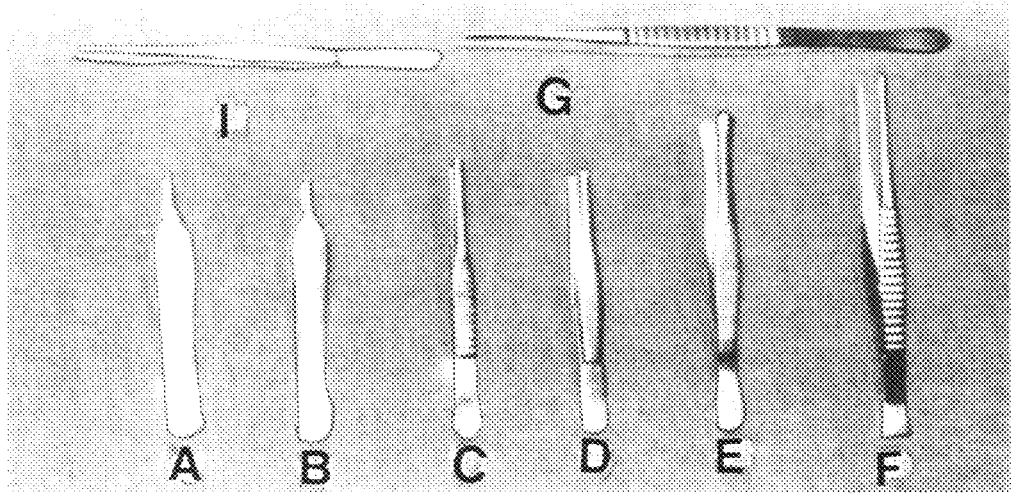
Prior Art Fig. 4
Non-perforating Towel Clamp Thumb Forceps: (A) Adson, (B) Brown-Adson, (C) Thumb w/teeth, (D) Bonnie, (E) Russian, (F) Cushing, (G) DeBakey, and (I) Dressing
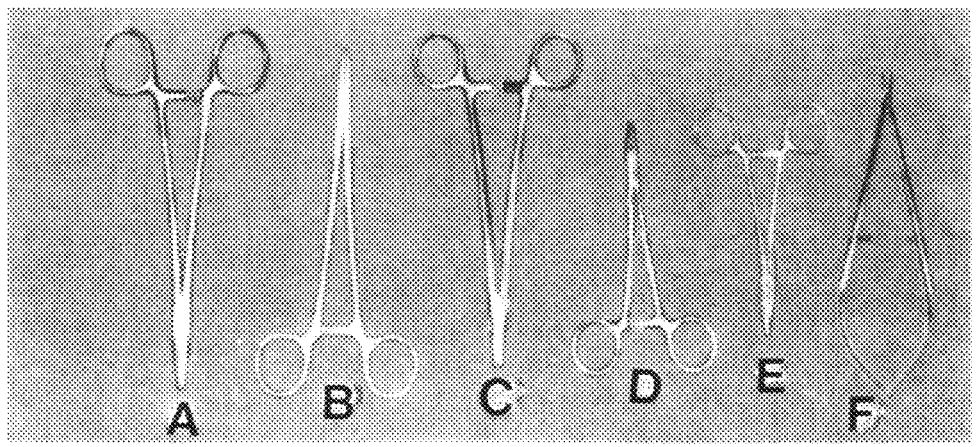
Prior Art Fig. 5
Needle Holders: (A) Mayo-Heagar, (B) Crile-Wood, (C) Olsen-Hegar, (D) Collier, (E) Webster, and (F) Castroviejo Prior Art Fig. 6
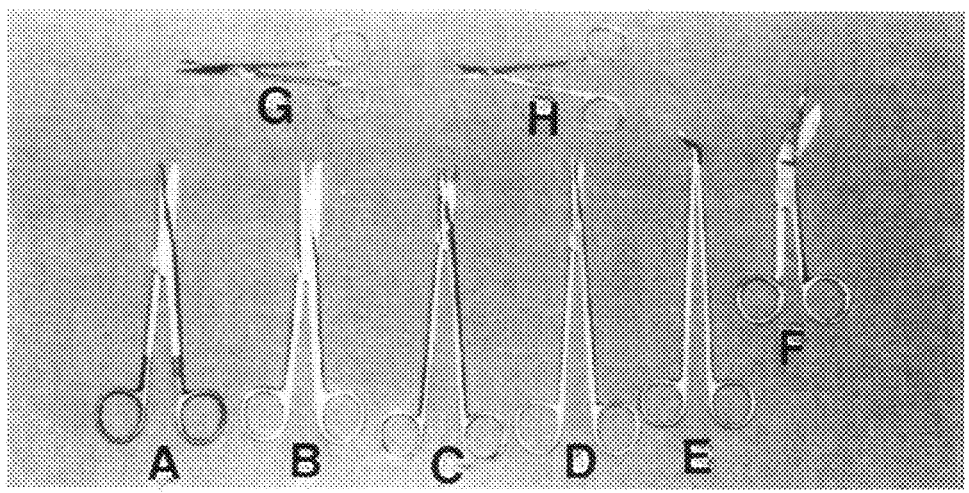
Scissors: (A) Mayo Dissecting Straight, (B) Mayo Dissecting Curved, (C) Metzenbaum, (D) Metzenbaum Delicate, (E) Potts-Smith, (F) Lister Bandage, (G) Iris Straight, and (H) Stevens Tenotomy
Prior Art Fig. 7
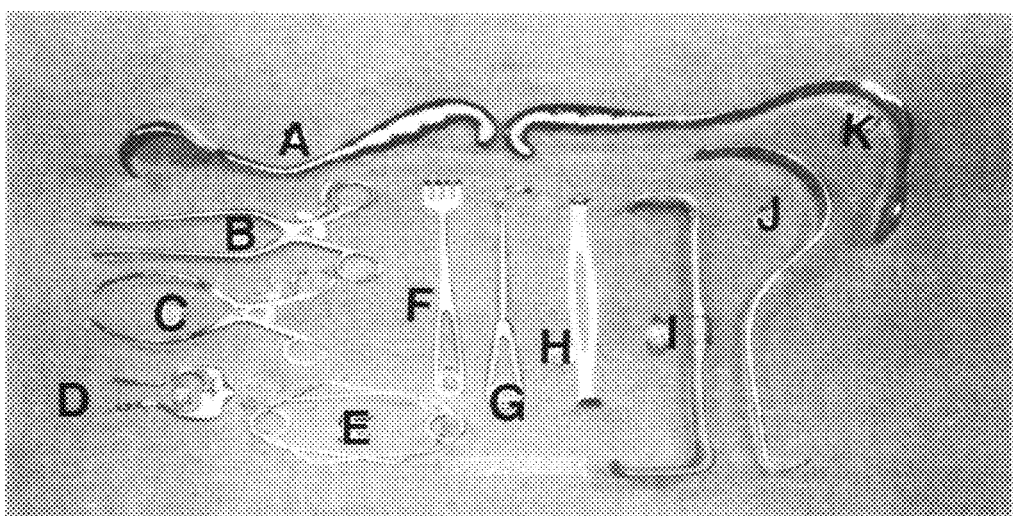
Retractors: (A) Mayo, (B) Cerebellum, (C) Gelpi, (D) Janson Mastoid, (E) Spring Wire, (F) Volkman Rake-Sharp, (G) Green Goiter, (H) Army-Navy, (I) Richardson-Eastman, (J) Deaver, and (K) Sweetheart

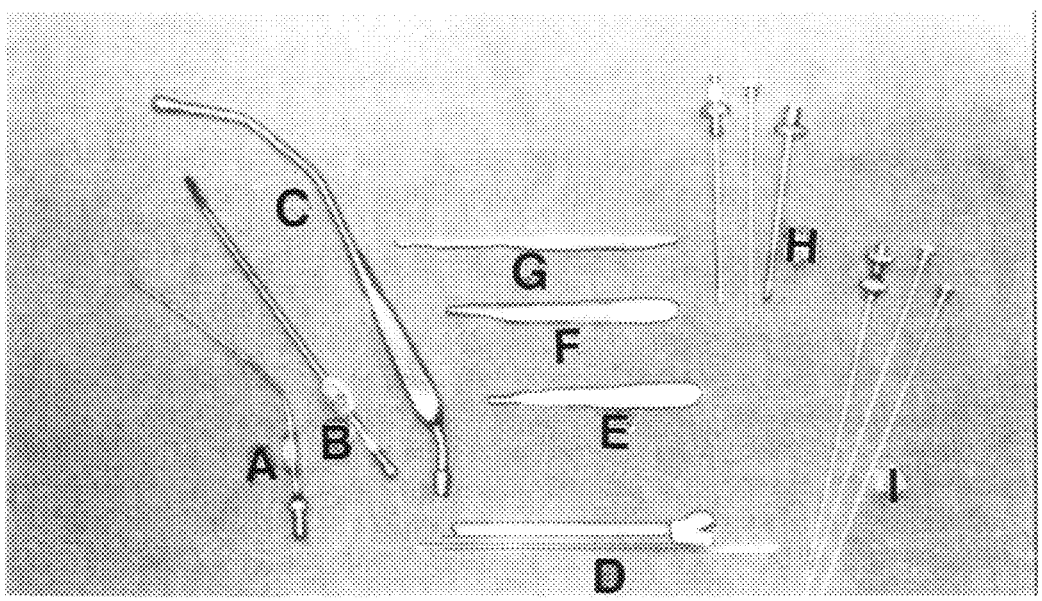
Prior Art Fig. 8
Miscellaneous Instruments: (A) Frazier Suction, (B) Rhoton Suction, (C) Yankauer, (D) Probe w/eye and Groove Director, (E) No. 3 Knife Handle, (F) No. 4 Knife Handle, (G) No. 7 Knife Handle, (H) Abrams Needle, and (I) Vim Silverman Needle Prior Art Fig. 9
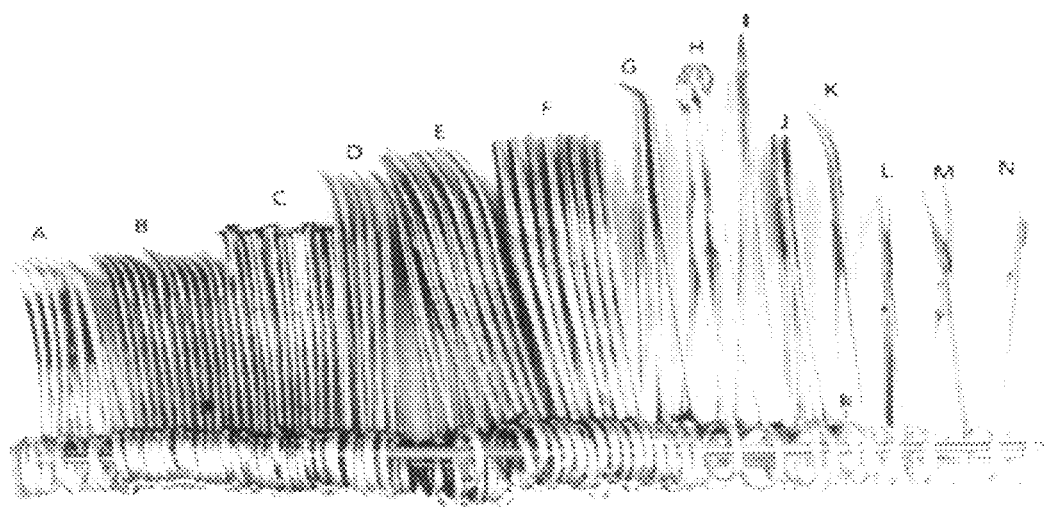
(A) Backhaus Towel, (B) Kelly Forceps, (C) Allis Intestinal Clamps, (D) Crile Forceps, (E) Carmalt, (F) Kocher Clamps, (G) Right Angle Clamps, (H) Forrester Sponge, (I) DeBakey Needle Holder, (J) Mayo-Hegar Needle Holder, (K) Curved Metzenbaum Scissors, (L) Straight Mayo Scissors, (M) Curved Mayo Scissors, (N) Curved Metzenbaum

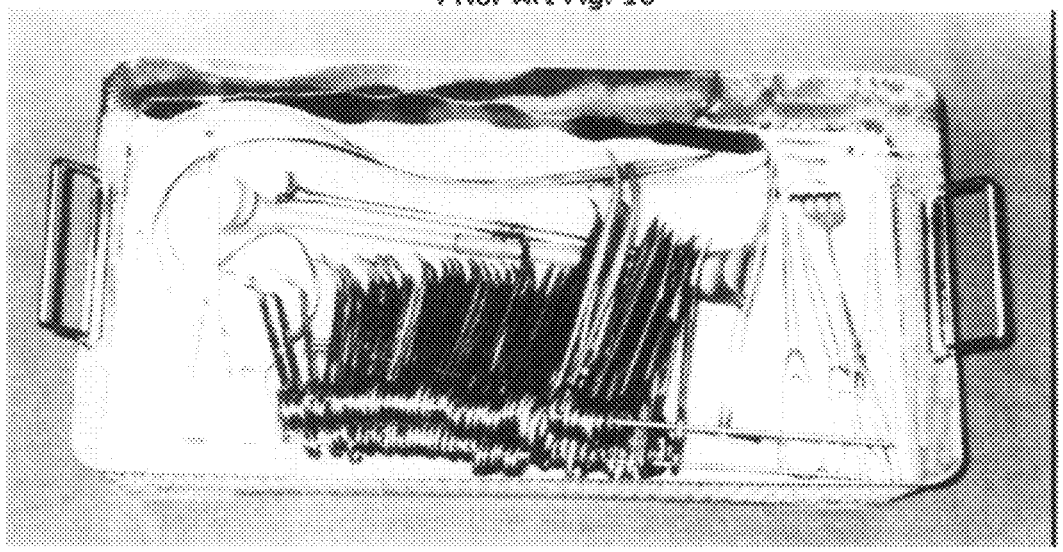
Prior Art Fig. 10

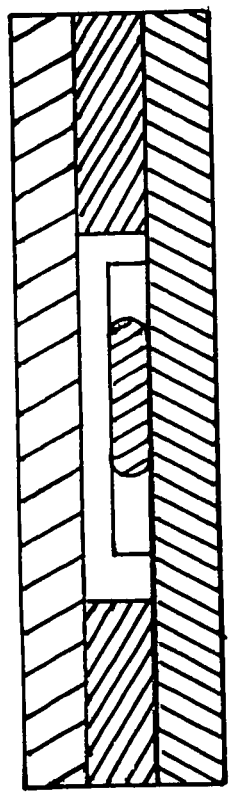
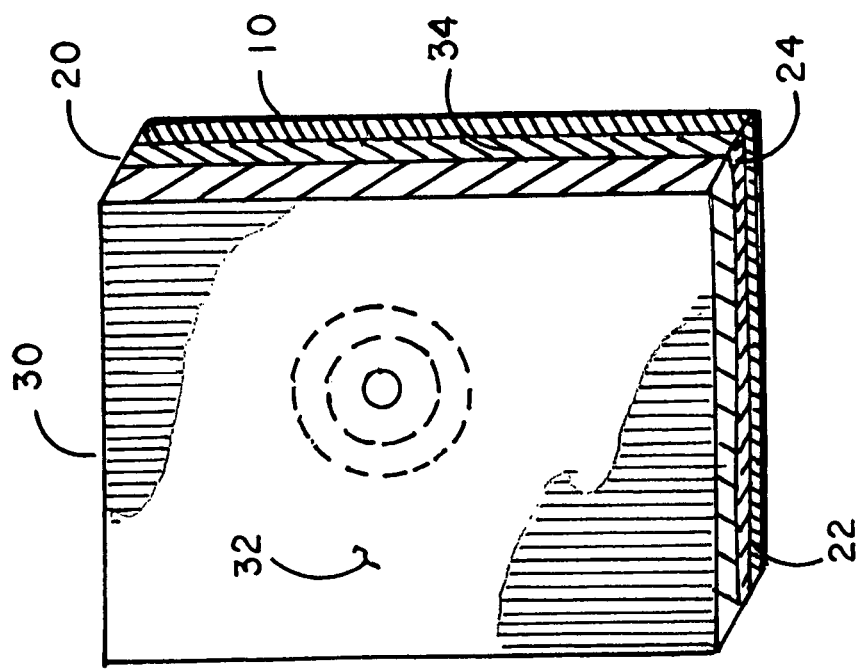

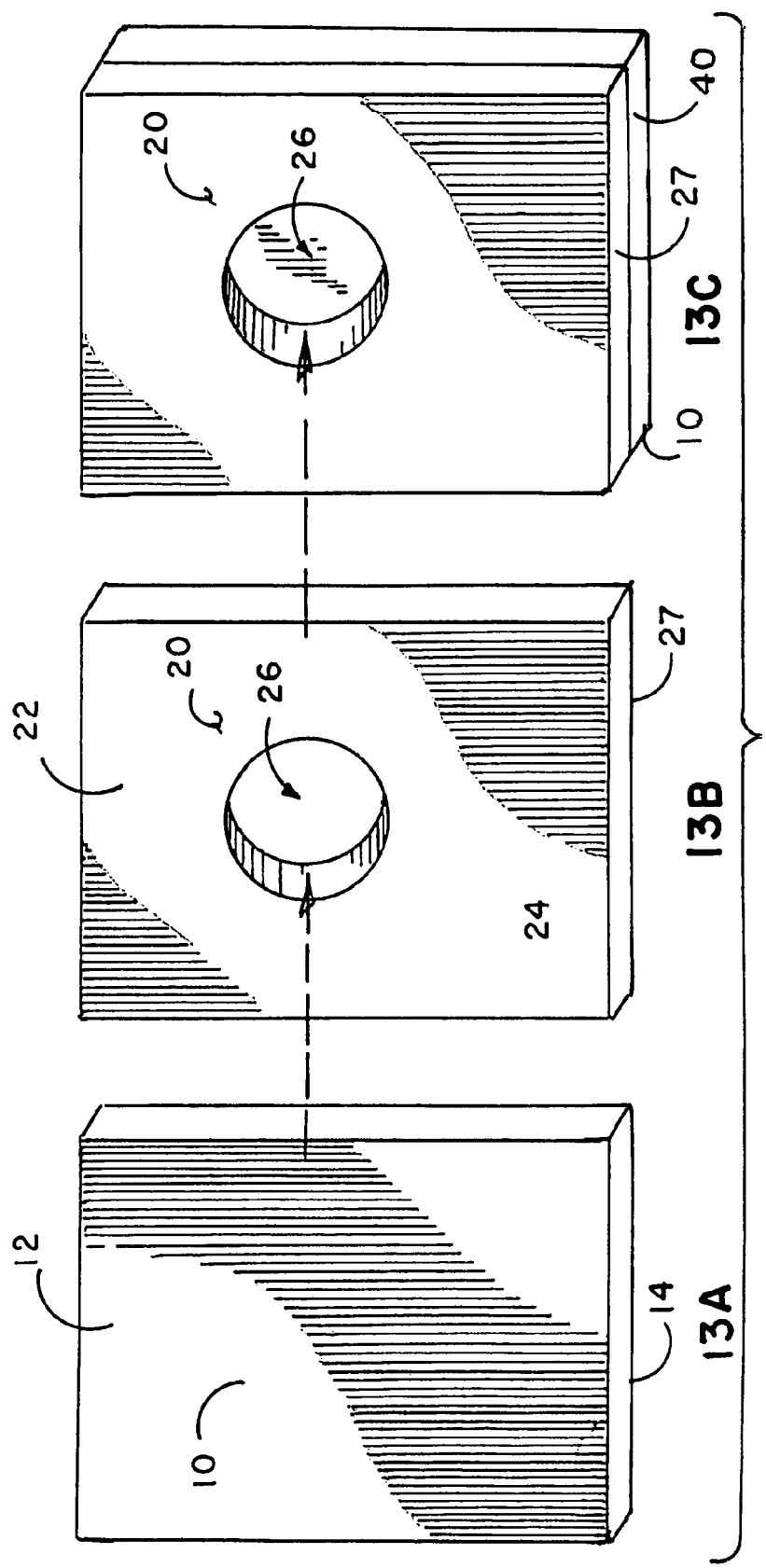

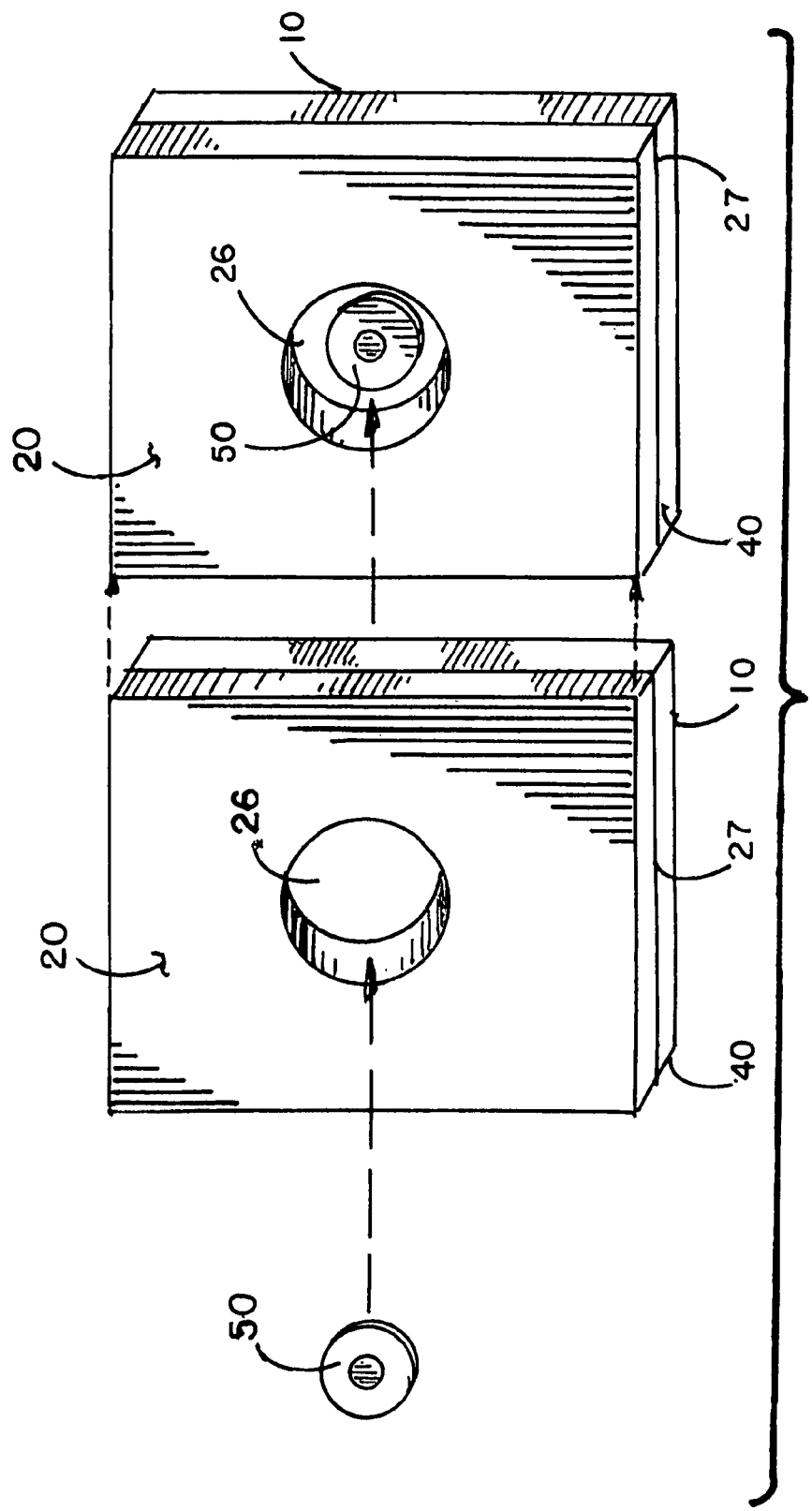

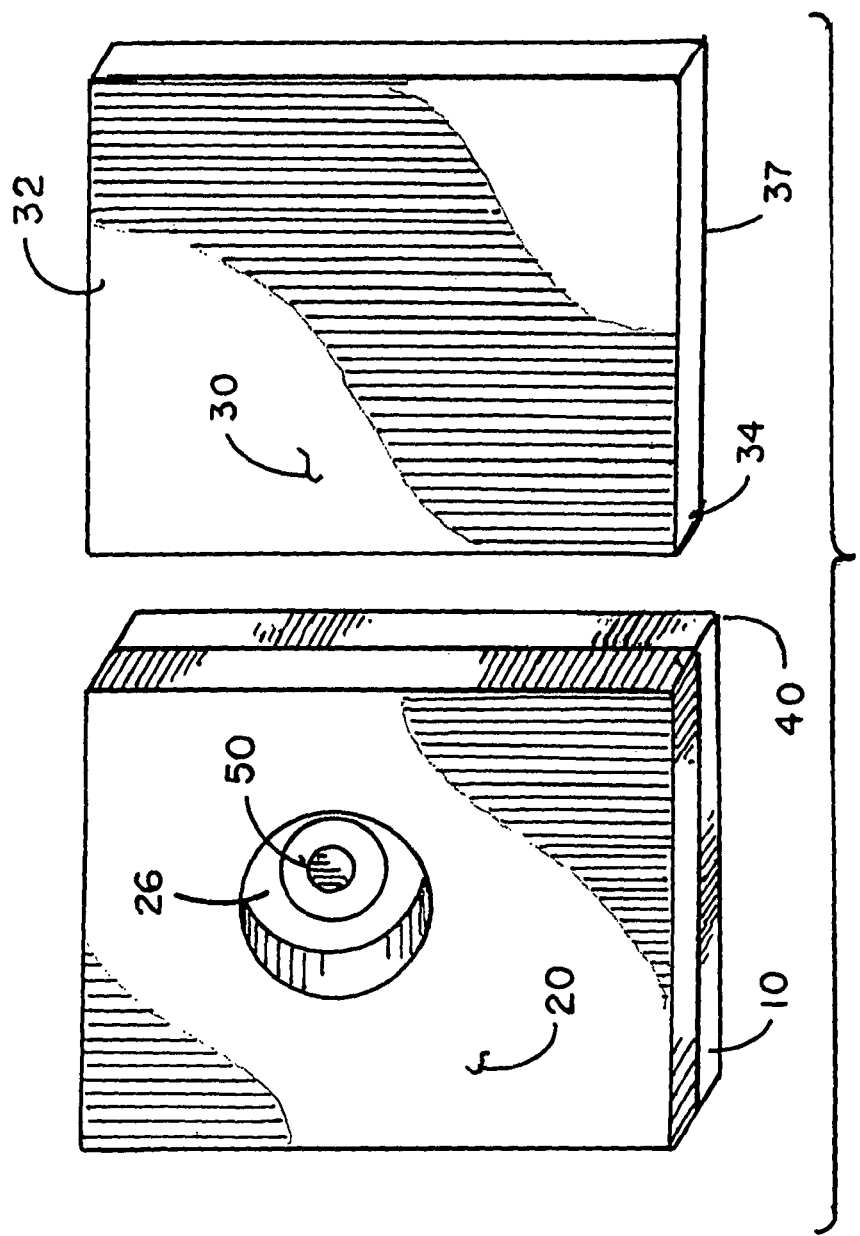

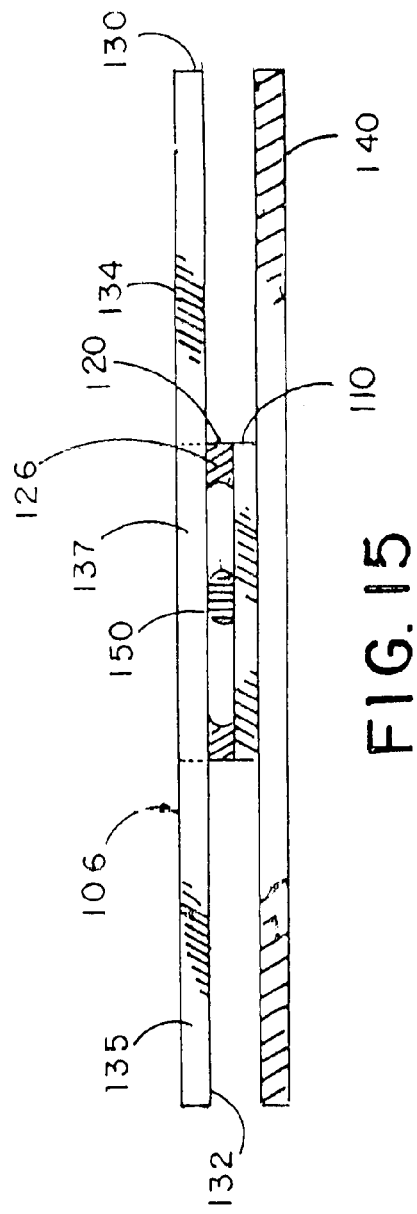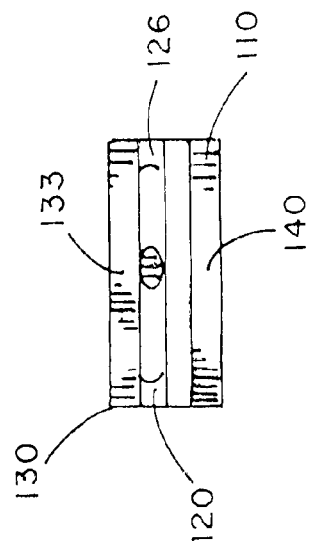

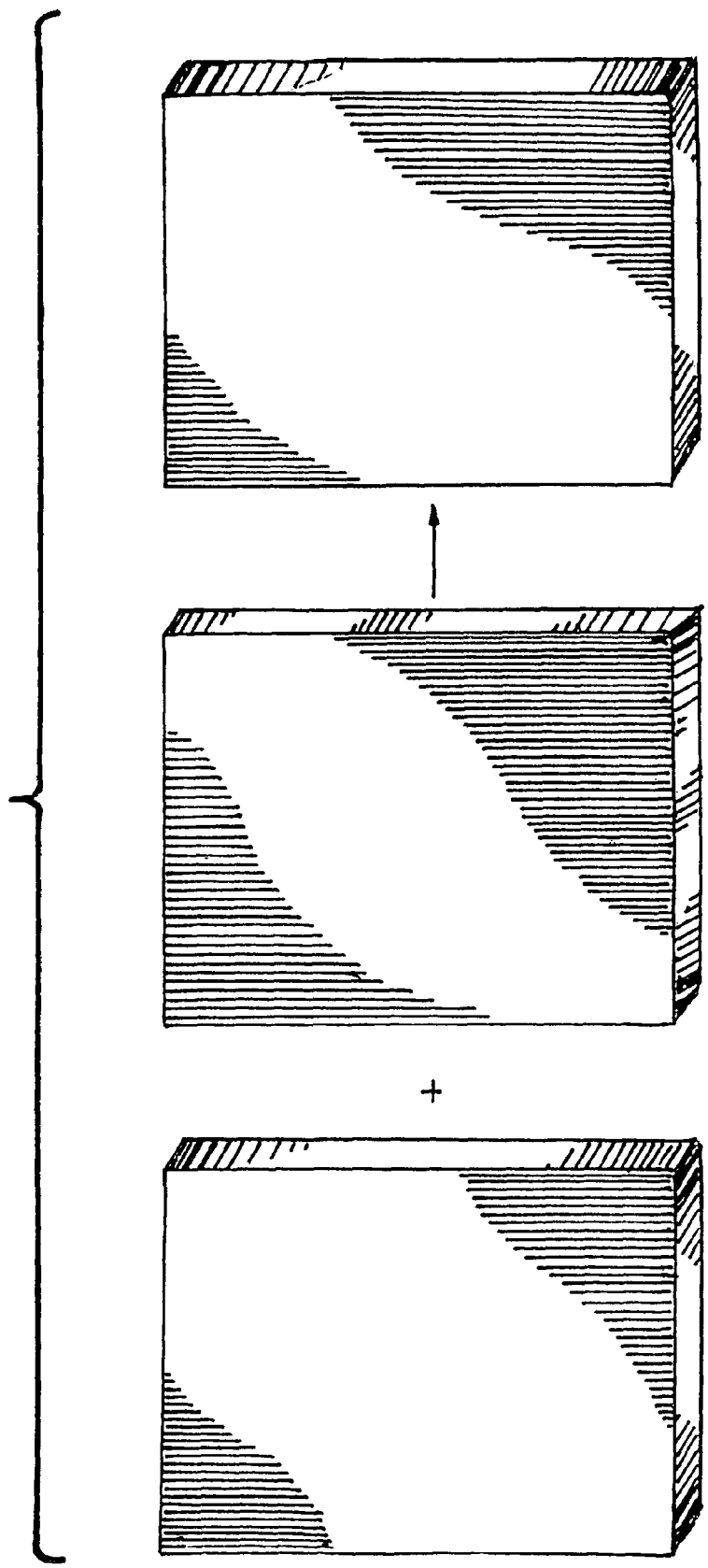

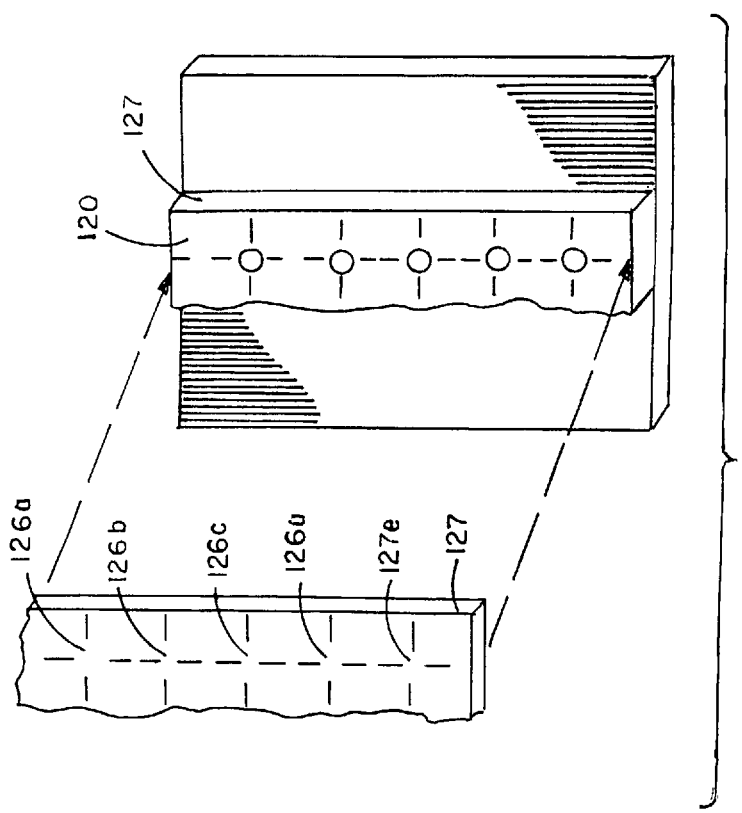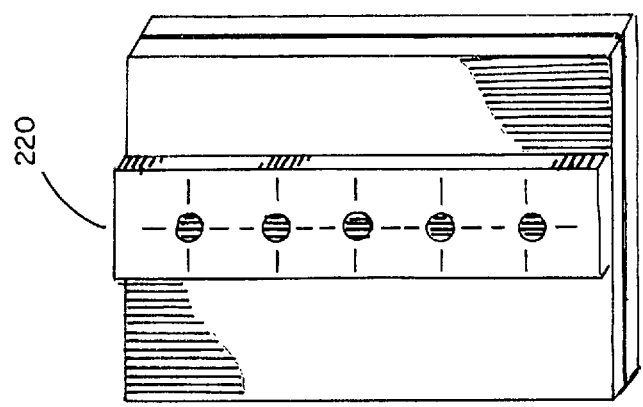

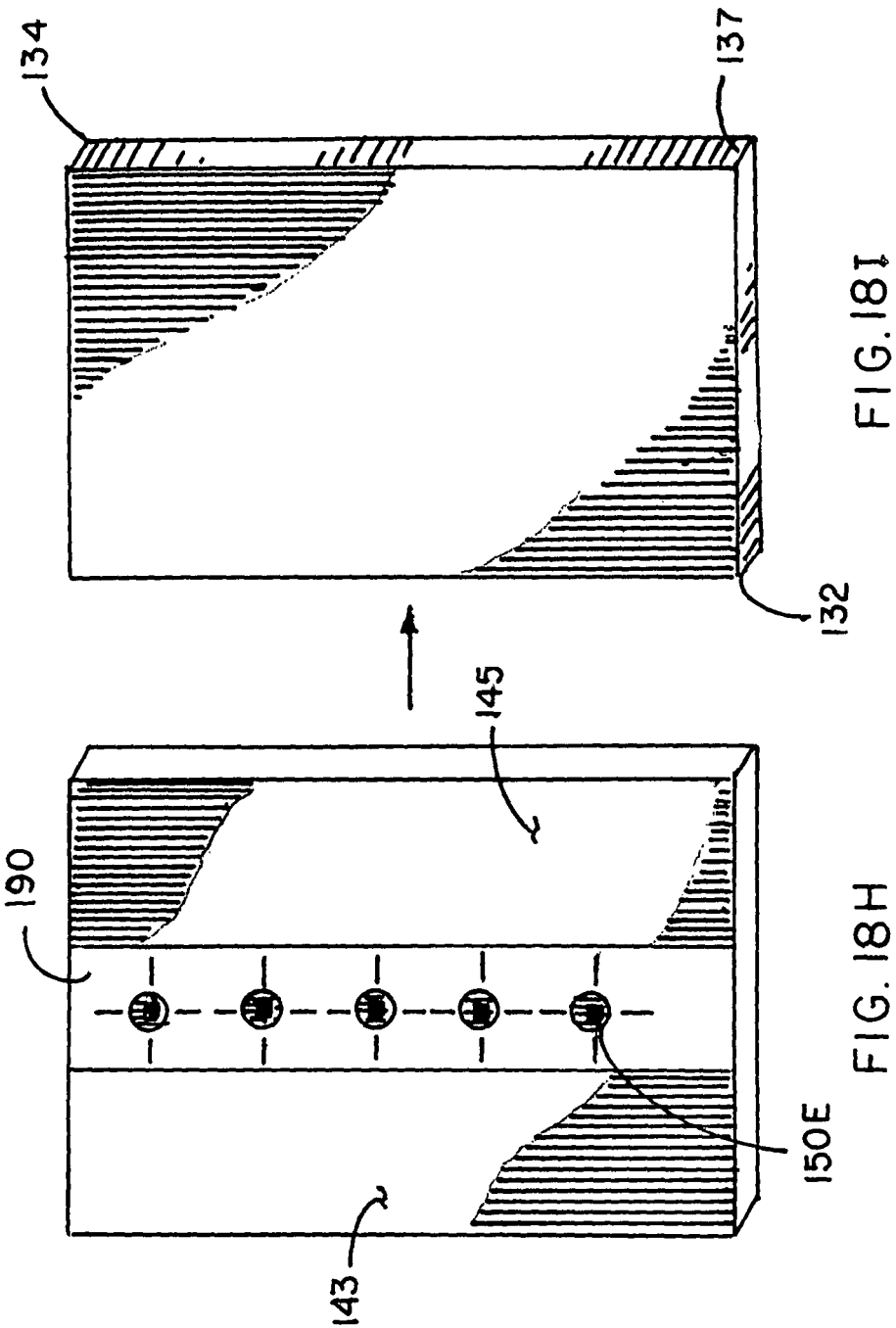

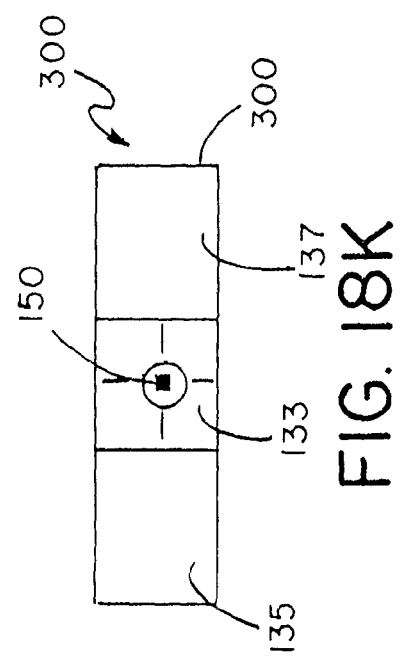
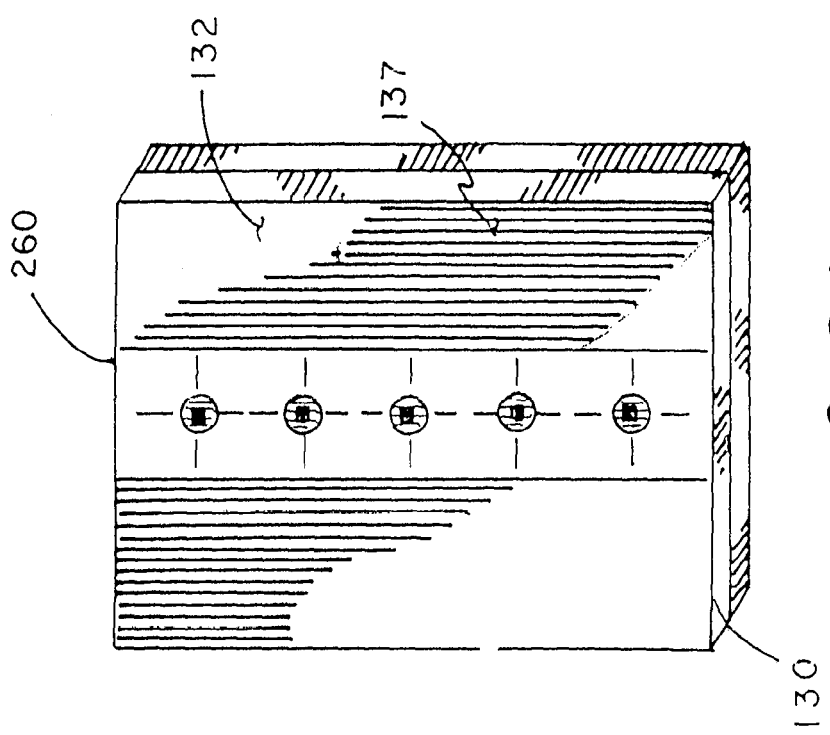

MILLIMETER-SIZED RECOGNITION SIGNAL BADGE AND IDENTIFICATION SYSTEM FOR ACCURATELY DISCERNING AND SORTING AMONG SIMILAR KINDS, SHAPES, AND SIZES OF SURGICAL INSTRUMENTS

FIELD OF THE INVENTION

The present invention is generally concerned with the application of Complementary Metal Oxide Semiconductor (CMOS) chip technologies which are electronically able to broadcast recognition signals for object identification and sorting purposes; and is particularly directed to the use of such CMOS chip technology for a millimeter-sized recognition signal badge and object identification system by which to differentiate and distinguish accurately among similar kinds, shapes, and sizes of surgical instruments and tools used today for performing a variety of human and veterinary surgical procedures.

BACKGROUND OF THE INVENTION

Surgical Tools and Instruments

Surgical tools and instruments intended for use in human and veterinary surgery are typically sorted and organized into tray arrangements by: (i) specified surgical procedure, (ii) surgeon preferences for a type and variety of instruments, and (iii) the particular anatomic area or part of the human body to undergo surgery. One exemplary instance of this organized arrangement sorting would be an instrument tray used by general surgeons specifically for human hernia repairs. That pre-arranged tray of particular surgical instruments will then be used for all manner of hernia repairs by each of the general surgeons at that hospital or clinic; or by one specific general surgeon at that particular hospital; or by both thoracic surgeons and general surgeons, each of whom perform hernia repairs at that hospital or clinic.

In addition, some arrangements of instrument trays are used for different types of surgeries beyond one specific procedure. As a result, each arranged instrument tray used at hospitals has many different kinds and types of similar instruments and tools that are critical for surgeons to perform their surgeries properly. Thus, some characteristics of the individual instrument present in hospital surgery instrument trays are:

That surgical instrument may be specific only to that tray;
That surgical instrument may also reside in other surgical trays;
That surgical instrument may be one in number or be several of the same in a single tray setup;
That surgical instrument may exist in several different styles, shapes, and sizes in any given tray arrangement.

A. The Range and Variety of Hand-Held Surgical Tools and Instruments

Hand-held instruments are still the most common type of surgical tool. Thus, it is vital and essential that all the general kinds and very similar alternative types of instruments be properly identified and distinguished by the surgical technician as to kind, size, and shape; and that the technician will be able to recognize the critical differences that separate and distinguish the different patterns, designs, and formats of similarly appearing instruments utilized for specific surgeries [see for example: Colleen Rutherford, *Differentiating Surgical Instruments*, 2nd Edition, F. S. Davis, 2011; Hinton & Allhoff, *Surgical Mayo Set-Ups*, 1st Edition, 2003; Goldman, Maxine A., *Pocket Guide to the Operating Room*, F A Davis Co, 2007; Maryann Papanier Wells, *Surgical Instruments: A Pocket Guide*, Saunders, 2010; and Shirley M Tighe, *Instrumentation for the Operating Room: A Photographic Manual*, Elsevier Health Sciences, 2011].

Thus, within the particular field of surgical instruments, the conventional "anatomy" of hand-held surgical instruments and tools is as follows: The structure of any typical hand-held hemostat or clamp includes jaws, box lock, shanks, ratchets, and finger rings; and the structure of all typical surgical scissors contain jaws, shanks, finger rings, and a screw. These conventional structural features are identified and illustrated by Prior Art FIG. 1.

In addition, tissue forceps used specifically for eye surgery will resemble and often be mistaken for tissue forceps used in general surgery—the only meaningful difference between the two types being the size of the instrument. The same difficulty hold true for retractors, needle holders, and many other kinds of surgical tools. The sole minor exception to this general rule would be the extremely unusual specialized instruments used for only orthopedic and dental surgical procedures Given the foregoing, these kinds of surgical instruments traditionally are separated into a series of conventionally recognized categories or classes, which are:

Haemostatic Forceps

These forceps can be called clamps, artery forceps, and hemostats. The main purpose of hemostats is to achieve hemostats (control of blood flow in the vessel). Most hemostats are available in different lengths, curved and straight, with serrated jaws. Some also have toothed ends. Illustrative examples of hemostats include the Mosquito, Kelly, Carmalt, Schnidt tonsil, and Kocher types; and these are individually visually presented by Prior Art FIG. 2.

Soft Tissue Forceps

Similar to haemostats, these forceps are used for holding and retracting soft tissue for longer periods. Characteristics include fine teeth or ridges on the jaws to provide a more delicate grip without trauma to tissue. They also consist of ring handles and box locks, as do the haemostatic forceps. Some typical examples are the Backhaus Towel, Allis Intestinal, Babcock Intestinal, Kocher Artery, Mixter Gall Duct, Kantorwitz Right Angle, and Forester sponge forceps; and these are visually presented by Prior Art FIG. 3.

Other Soft Tissue Forceps

Thumb Type

Thumb forceps do not have box locks or ring handles but rather have spring handles which are held closed by the thumb and finger pressure. Sometimes this type of forceps is referred to as dressing forceps when the jaws are serrated and the instrument is used to grasp delicate tissue or wound dressing. A heavier version of this type of forceps is referred to as thumb tissue forceps used for grasping heavier tissue where the teeth will provide a more secure grasp. A representative range of exemplary thumb forceps are the Adson, Brown-Adson, Hudson, Dressing, Tissue Forceps with Teeth, Russian, Cushing, and DeBakey varieties; and these are individually visually presented by Prior Art FIG. 4.

Needle Holders

Sometimes referred to as needle drivers, this type of instrument is mainly ring handled, similar to hemostats but with smaller jaws which are shorter and thicker. Needle holders hold needles which are attached to sutures. These instruments are also available in a variety of lengths and styles and may be curved or straight. Needle holders have inserts in the jaw to prevent excessive wear of the instrument. These inserts are mainly made from tungsten carbide granules in a cobalt or other metallic paste. Needle holders with tungsten carbide inserts are normally identified with gold plated handles. The inserts can be replaced as they wear down, which prolongs the life of the needle holder and defrays the replacement cost of an entire instrument. Some examples of needle holders are: Mayo-Hegar, Crile-wood, Olsen-Hegar, Collier, and Webster.

Needle holders can also have spring handles which allow the user maximum results with minimum rotation of the wrist and hand. Most spring handled needle holders will have a lock or catch to secure the needle and are used in surgical procedures requiring delicate suturing in tight or poorly exposed areas. Spring handled needle holders may also contain replaceable inserts. An example of a spring handled needle holder is a Castroviejo, 7 or 9 inch. As merely illustrative of these diverse varieties, Prior Art FIG. 5 visually presents the Mayo-Heagar, Crile-Wood, Olsen-Hegar, Collier, Webster, and Castroviejo needle holders respectively.

Scissors

A large variety of scissors are utilized in the surgical operating room which include many lengths, styles, curved, straight, sharp, and blunt scissor types. In general, curved scissors are used to cut and dissect tissue; while straight scissors are used for cutting sutures and any tissue when a smooth, straight cut is desired—such as a damaged nerve or blood vessel. Scissors can also be used for probing, dissecting, and spreading tissue. However, such surgical scissors should never be used to cut paper or tubing; instead, bandage scissors are to be utilized for this purpose.

The major types of scissors today include: Mayo scissors, identified by heavy curved or straight blades with rounded tips; Metzenbaum (Metz) scissors, similar to Mayo only lighter in pattern and more delicate; Iris (dissecting) scissors, resembling cuticle scissors but more delicate in style. Operating or general use scissors can be used for cutting sutures and gauze. The heavier types are used for cutting fine wire sutures and are identified by angular blades with serrated edges with a grove for holding the wire as it is being cut. Scissors may also have tungsten carbide cutting edges which provide finer cutting with longer lasting wear. Scissors with tungsten carbide inserts are identified by gold plated ring handles.

A representative variety of different scissor types are illustrated by Prior Art FIG. 6; and these visually appear therein as the Mayo Dissecting Straight, Mayo Dissecting Curved, Metzenbaum, Metzenbaum Delicate, Potts-Smith, Lister Bandage, Iris Straight, and Stevens Tenotomy scissors respectively.

Retractors

Many varieties and sizes of retractors are available, and the use of specific retractors will largely depend on the type of surgical procedure being performed. Retractors are used for holding the incision open to provide exposure to the surgical site. Smaller types held by the fingers or hand retract skin and subcutaneous tissue in shallow surgical areas. Larger, heavier models retract muscle tissue and organs in deeper surgical sites. Some retractors are held in place by an assistant while the surgeon completes the procedure, while self-retaining retractors require no assistant to hold them. Self-retaining retractors are held open by their own action and may be used in conjunction with the hand held retractors. Common examples of different retractors are individually illustrated by Prior Art FIG. 7; and these appear as the Richardson—Eastman, Mayo, Jansen Mastoid, Weitlaner, Cerebellum, Gelpi, Volkman Rake, Green Goiter, Army-Navy, and Deaver retractors respectively.

Biopsy Needles

Biopsy needles are used for the removal of fluids or tissue for the purpose of microscopic examination. Many sizes and varieties of biopsy needles are available in stainless steel, as well as disposable varieties. Disposable needles do not require sharpening and inspection as do reusable biopsy needles. Reusable biopsy needles must be sharp and free of burrs to assure proper function and avoid damage and trauma to tissue. Representative examples of biopsy needles include the Abrams Pleural Biopsy Punch and the Franklin-Silverman Biopsy Needle.

Suction Tubes

Suction tubes are used for the removal of blood, tissue, and fluids from the surgical site to allow surgeons a clear view of the anatomical structures during the operative procedure. Several types of tubes can be used, depending on the procedure, and many will have removable tips that require close attention during the cleaning process. The tube is attached to suction tubing connected to a graduated reservoir to measure the amount of fluid removal. Common examples of such different suction tubes are the Pool Abdominal, Frazier, Rhoton, and Yankauer Suction Tubes.

Other Miscellaneous Items

Probes are some of the miscellaneous instruments required for use in surgery or some clinical procedures. Probes may be used to explore the depth and direction of body ducts, sinuses, or cavities. They may also be used as an aid in dilating or irrigating an area of the body, such as a duct. Also knife handles are available in several styles and require disposable blades that may be changed frequently during the surgical procedure. Typical examples of probes and knife handles are visually illustrated by Prior Art FIG. 8; and individually appear there as a probe with eye, optical probes, and knife handles numbers 7, 4, and 3 respectively.

B. Surgical Instrument Processing Procedures

The proper processing of surgical instruments and tools always involves:

(i) Instrument decontamination, cleaning, and safe handling;
(ii) Surgical tray arrangement setup; and
(iii) Sterilization of arranged instruments within a tray.

All surgical instruments set up within the operating room will require processing, regardless of their use during the surgical procedure. Instrument sets opened but not used during surgery still require processing through an ultrasonic washer/sterilizer or washer/decontaminator. The hospital technician also inspects the instruments for tissue or bone deposits remaining in the teeth or grooves; and will remove all tissue and debris by holding the instrument under water and physically scrubbing the contact areas with an instrument brush.

Instrument washing via automatic washers is the next step in the process. A drying cycle is typically set to assure the washed instruments will dry completely and not emerge wet after the wash cycle. If the instruments do not dry completely, steps should be taken to dry the instruments. Utilizing an air hose to blow excessive moisture from the instruments or manually drying with absorbent material are recommended.

The recommended steps which follow in the preparation area for instrument set arrangement in trays then generally are:

(a) Separating and removing instruments that require repair or replacement.

(b) Setting up a tray assembly of instruments in accordance with specified requirements.

(c) Preparation for instrument tray sterilization.

Instrument trays are typically assembled and arranged by a trained surgical technician using a detailed photo procedure by which to identify, separate, and differentiate among many kinds, shapes, styles, and sizes of surgical instruments. Ring-handled instruments of various kinds are routinely placed on a stringer, instrument rack, or other means that allows the instruments to remain in an open or unlocked position. This will allow the sterilant (sterilizing medium and process) contact to all surfaces. Instruments with multiple parts (such as a Balfour retractor or tonsil snare) are disassembled to allow all parts exposure to the sterilant.

Surgical instruments are individually identified and placed on a stringer, tray, or set in a manner to prevent damage to the instruments; and will provide easy, orderly, and direct access by the operating room scrub nurse. Prior Art FIG. 9 shows a typical alignment of string instruments on a tray as a set collection.

As shown by Prior Art FIG. 9, it will be appreciated that the scissors can be turned in, toward the center of the stringer, as long as the tips do not touch another instrument. Also, the shorter instruments are at the end of the stringer, with the longer toward the center. This arrangement order aids the operating room nurse since the instruments at either end of the stringer will be used first during the procedure, with progression to the longer instruments as the surgery proceeds.

Knife handles, tissue forceps, pickups, probes, etc., may be wrapped in medical grade paper or placed in pockets to allow easy access to the items. Other items, such as gauze, cotton tipped applicators, etc., should be packaged separately from the instrument sets to allow proper exposure to the sterilant.

The arranged collection of prechosen surgical instruments is traditionally placed in a shallow tray with a perforated bottom. The prechosen instruments are placed in such a manner to allow contact to all surfaces during the sterilization cycle. Large heavy items, such as retractors, should be placed on the bottom of the tray. The stringed instruments should go in last, to assure no heavy item will be placed on top that may damage the delicate tips. Prior Art FIG. 10 illustrates the manner of proper instrument placement in the tray.

After the instrument set is assembled in a tray, a specific content inventory list is made (also bearing the initials of the technician who prepared the set) and added to the tray. This verification inventory list serves as a double check for the technician that the correct and proper instruments are in fact present in the set collection. The prepared and verified instrument set is then wrapped with muslin or nonwoven disposable wrap, or placed into a container system; and then placed on a sterilization rack in an upright manner.

The prepared instrument trays are then placed on the sterilization rack in such a manner as to allow proper circulation of the sterilant. Typically, large surgical trays are placed on the bottom rack, while smaller trays or sets and individual packages are placed on the top rack.

After sterilization by any effective method—i.e., steam, dry heat, gas, or light irradiation—is completed, the sterilized tray of instruments is then marked with the name of the set, and with the initials of the technician who actually assembled the item.

Conventional Surgical Instrument & Tool Identification Systems

For operating room purposes, hospitals and clinics have many different types of prepared surgical trays, many of which require specific kinds, shapes, and sizes of instruments used for surgery. In each instance, the correct choice of requisite instruments arranged in the proper order must exist. Consequently, in order to keep track of which arrangement a particular surgical instrument or tool rightly belongs to, several instrument identification techniques have been attempted over time, which have had only modest degrees of success.

Most commonly known among these conventional instrument identification techniques are two particular examples:

(1) Human Eye Visible Identification Tapes

In some hospitals and clinics, a special highly-visible tape appearing in different color and shape combinations is affixed to the surface of the individual instrument or tool. The particular color and shape of the tape allows for quick human eye identification by those hospital workers who assemble the instruments into surgical tray arrangements. The highly-visible tape has special durability and adhesion characteristics which allow the tape to survive the repeated harsh washing/drying cycles and the repeated severe sterilization processing that the surgical instruments must endure before being fit for use again in surgery.

Nevertheless, because the tape label is directly exposed to a cycle of surgical use, then to the harsh washing/drying cycles, and finally to severe sterilization repetitiously over and over again—the original color codes fade and become blanched, and the original configured shapes fray and shred over time. In addition, the system is entirely dependent upon the human eye and the human mind for identification; and the human technician must still see the tape correctly and then refer to a written listing of color codes and configurations before any accurate identification can be made. Furthermore, manual check-off lists for instrument tray assembly is very time consuming, and plagued by inaccuracies. Also, hospitals have to spend considerable resources in developing human instrument specialists for the job of assembling specific surgical instrument trays.

(2) Barcode Label Identification Systems

There have been multiple attempts to develop a reliable traditional linear and two-dimensional labeling system by which to identify and distinguish accurately among similar kinds, shapes and sizes of surgical instruments. However, although now widely accepted in commerce and commonly used in inventory control merchandising, there are many major obstacles which meaningfully bar and prevent a functional use of barcode labels with surgical instruments and tools; which include all of the following:

To be operative, the barcode identification label must be placed on a relatively flat surface which is fully exposed and is visibly viewable—or the existing scanning technology will not be able to read the bar code, as the scanner/reader cannot get a complete or accurate image of the complete barcode itself. However, many surgical instruments and tools have very little exposed surface area that is flat or a planar surface.

The traditional barcode identification label is a modestly large strip which often is 1-2 inches in length; but many surgical instruments are quite small in their dimensional sizes. Two dimensional barcodes, which are smaller, also have similar problems as they need to be scanned in two dimensions on a flat surface, which will not work on the small round dimensions of many surgical instruments.

The barcode label must be placed on the instrument in such a manner that the label does not interfere with the points of instrument contact used at the anatomic surgical site of the patient.

The barcode label is traditionally most often applied to the handles of an instrument or the grips of a tool. However, many surgical instruments and tools have rounded handles or oval shaped grips.

For any barcode label system to be useful in identifying surgical instruments in trays, all the pre-chosen instruments of each respective tray must be able to be scan-identified, otherwise the desired tray arrangement will not be accurately assembled.

For these reasons, hospitals and clinic have generally been compelled to apply barcode identification systems only at the "pallet" or assembled tray level; but have been markedly hampered and routinely disappointed when attempting to apply barcode identification labels directly to the individual instruments assembled within a single surgical instrument tray. As a result, the current use of such barcode identification systems still cannot and does not avoid the presence of a wrong or mis-chosen instrument in surgical instrument tray assemblies; and the problem today still remains a serious and continuing challenge waiting to be solved.

Complementary Metal Oxide Semiconductor (CMOS) Chip Technology

A complementary metal oxide semiconductor (CMOS) is an integrated circuit design on a printed circuit board (PCB) that uses semiconductor technology. The PCB has microchips and a layout of electric circuits that connect the chips. All circuit boards are typically either CMOS chips, N-type metal oxide semiconductor (NMOS) logic, or transistor-transistor logic (TTL) chips. The CMOS chip is most commonly used, as it produces less heat and requires less electricity than the others. See for example: David Harris & Neil Weste, *Integrated Circuit Design*:4E:, Pearson, 2013; Thomas H Lee, *The Design of CMOS Radio-Frequency Integrated Circuits*, Cambridge University Press, 2003; R. Jacob Baker, *CMOS Circuit Design, Layout, and Simulation*, Institute of Electrical and Electronics Engineers, 2007; and Razavi, *Design of Analog CMOS Integrated Circuits*, McGraw-Hill College, 2000.

CMOS technology is used in static RAM, digital logic circuits, microprocessors, microcontrollers, image sensors, and the conversion of computer data from one file format to another. Most configuration information on newer CPUs is stored on one CMOS chip. The configuration information on a CMOS chip is called the real-time clock/nonvolatile RAM (RTC/NVRAM) chip, which works to retain data when the computer is shut off.

Operationally, CMOS technology holds different electrical components together within one circuit or in multiple circuit groupings. Each individual circuit performs a specified purpose that increases a PC's proficiency. The two most important features of CMOS integrated circuit design are low-static electrical power consumption and a marked resistance to high levels of electronic noise.

When integrated onto one silicon chip, the CMOS integrated circuit design typically employs a combination of P-type and N-type metal oxide semiconductor field effect transistors (MOSFETs). These MOSFET circuits allow the implementation of logic gates, thereby forming paths to the output from the source of the voltage or the ground. It is noteworthy that the integrated circuits of CMOS chips are composed of millions of transistors that collectively allow a high density of logic functions. Moreover, when compared to a conventional logic controller, the CMOS integrated circuits use half the electrical power needed to operate dynamic and static positions.

Also, the CMOS integrated circuits conduct many logic functions that operate only when a unit is being used. This process dramatically reduces the amount of current required to maintain a certain voltage. Processors that use CMOS-based transistors are also more efficient and run at very high speeds without getting too hot. Furthermore, CMOS the CMOS integrated circuits are powered by lithium batteries which can last two to ten years in duration. However, once a lithium battery goes dead, the entire CMOS chip must be replaced.

CMOS chip technologies possess the particular characteristic of being able to signal-broadcast unique data and information—such as a singular recognition number which identifies each individual chip. Presently known CMOS chip technologies however encompass and include several different varieties of apparatus.

Electronic Transponders

Electronic transponders are useful in a wide variety of applications as a means by which to store data and transmit information on-demand. A transponder functions by receiving an electronic transmission request and, in turn, subsequently transmitting an electronic signal response. Typically, this response is an identification code signal, which often includes an identifying serial number. See for example: IEE Colloquium on *The Use of Electronic Transponders in Automation* (Digest No. 23), 15 Feb. 1989; Klaus Finkenzeller, Kenneth Cox & Dörte Müller, *RFID Handbook: Fundamentals and Applications in Contactless Smart Cards, Identification and NFC (Near Field Communication)*, John Wiley & Sons, Incorporated, 2010; *Operator's manual: transponder set, forward air control* [AN/PPN-18 (NSN 5895-00-579-4560)], Headquarters, Dept. of the Army, 1991; *Early performance of the 12-GHz, 200-watt transmitter experiment package in the Communications Technology Satellite*/Lewis Research Center, National Aeronautics and Space Administration, Springfield, Va., 1977.

Early constructions of electronic transponders supplied the necessary electric power for operation by way of an internal battery or a solenoid coil. However, batteries and solenoids are relatively bulky items; and therefore require the size of electronic transponders to be quite large in its minimal dimensions and volume.

Also, all electronic transponders require an antenna in order to broadcast its identification information signals; and this antenna must generate and broadcast a RF signal far enough in distance and strong enough in intensity to be received and demodulated by a remotely located receiver. The presence of the requisite antenna, however, further increases the overall size of the transponder.

Today, transponders are generally used for a variety of purposes ranging from identification of wildlife to electronic article surveillance. Most typically, transponders utilize a radio frequency identification (RFID) system which operates without need for any visual contact. For example, electronic transponder surveillance systems routinely employ a closed loop of a conductive substance that responds to a generated radio frequency (RF) field. These electronic surveillance transponders—also called "tags" owing to their capability of protectively labeling a consumer item to prevent shoplifting—are then deactivated manually when the product is purchased. In addition, for purposes of maintaining merchandise inventory control, such electronic surveillance systems may also transmit a short description of the particular item to which the tag is affixed.

Yet, despite their overall bulk volume and relatively large dimensions, transponders are employed for some unusual and unexpected applications. For example, electronic transponders aid in the detection of bio-molecules in samples when performing solid-phase assays [see for example: U.S. Pat. Nos. 5,641,634; 5,736,332; 5,981,166; and 6,001,571 respectively whose individual published texts are expressly incorporated by reference herein]. In such bio-applications, transponders are used for determining the sequence of nucleic acids; and for screening chemical compounds; and for performing multiplex assays for nucleic acids. However, when used in chemically hostile environments such as solid-phase assays, the external antennas and power sources utilized in electronic transponders must be carefully protected. Consequently therefore, the entire transponder unit, including the power source and antenna, is often enclosed in a sheath of protective material, such as a glass bead. Unfortunately, such protective enclosures merely add more dimensional size and greater volume to the previously existing bulk and girth of the transponder unit.

RFID Transponders

One recognized class of CMOS technology is radio frequency identification data (RFID) circuitry—an automatic identification technology whereby digital data encoded in a transponder or RFID "tag" is captured by a remotely located reader using radio waves. RFID technology has been conventionally known and used since about 1970; but it has generally been too cumbersome and expensive to use on a large scale, and thus has not been a commercial success to date.

In its earliest applications, the $1^{st}$ generation of RFID tags were used to detect and track large-sized tangible items that had to be shipped over long distances (such as livestock, railroad cars, and airline freight). These $1^{st}$ generation radiofrequency labels were all 'inductively coupled RFID tags'—i.e., very complex units formed of metal coils, antennae and glass; but which lacked any internal power source. As then designed, such inductively coupled RFID tags were powered by a magnetic field generated by a separate, but closely located, discrete RFID reader which generated an external magnetic field and inducted electric current flow within the tag components. The term "inductively coupled" refers to this process wherein the magnetic field of the RFID reader inducts an electric current in the tag circuitry.

Subsequently, in an attempt to lower the RFID technology's prohibitive commercial cost of manufacture, a $2^{nd}$ generation radiofrequency transponder was created known as the 'capacitively coupled tag'. These $2^{nd}$ generational improvements were meant to be disposable RFID tags that functioned as universal identifiers and were made for attachment to less expensive merchandise that required shipping. All 'capacitively coupled tags' use conductive carbon ink instead of metal coils to transmit data. Typically, the conductive carbon ink was printed on paper labels and were to be scanned by external readers located nearby.

Historically, Motorola's BiStatix RFID tags were the commercial frontrunners of this capacitively coupled format. These Motorola tags used a silicon chip that was only 3 millimeters wide and stored 96 bits of information. However, this $2^{nd}$ generation tag technology never was accepted with retailers, and the commercial production of BiStatix RFID tags ended in 2001.

The most recent innovations in the RFID tag industry are a $3^{rd}$ generational tag which encompasses and exists in not less than three structurally different construction formats. These three construct variants are: The active, semi-passive, and passive RFID tag formats.

Active and semi-passive RFID tags each use internal batteries to power their electronic circuits. An active RFID tag uses its battery power to broadcast radio waves to a remotely located reader/detector; whereas a semi-passive RFID tag relies on the remote reader/detector to supply the initiating radio signal for the tag to respond. The purpose of the internal battery in the semi-passive tag is to boost the effective operating range of the tag and to support additional feature—such as operation with lower radio signal strengths and sensing operations that require continuous power. Data from active and semi-active tags collected by remotely located readers/detectors is then passed through one or more communication interfaces (cable or wireless) to host computer systems; and is then passed to computer systems for decoding, interpretation, storage, and action. Alternatively, electric power may be supplied externally—e.g., by means of a car battery.

Some representative examples of active RFID tags are described by U.S. Pat. Nos. 4,207,468; 4,399,437; and 4,333,072. For comparison purposes, useful information and meaningful descriptions of semi-passive RF tags are provided by the following publications: J. Yeo, S. G. Moon and J. Y. Jung, "Design of Antennas for a Battery-assisted RFID Tags with a Thin and Flexible Film Battery," Microwave and Optical Technology Letters, Vol. 50(2), February, 2008, PP. 494-498; Hequn Chu, Guangmin Wu, Jianming Chen & Yumei Zhao, "Study and Simulation of Semi-Active RFID Tags Using Piezoelectric Power Supply for Mobile Process Temperature Sensing", Proceedings of the 2011 IEEE International Conference on Cyber Technology in Automation, Control, and Intelligent Systems Mar. 20-23, 2011, Kunming, China; Thomas Plos, Manfred Aigner, Thomas Baier, Martin Feldhofer, Michael Hutter, Thomas Korak, & Erich Wenger, "Semi-Passive RFID Development Platform for Implementing and Attacking Security Tags", International Journal of RFID Security and Cryptography (IJRFIDSC), Volume 1, Issues 1-4, March-December 2012

Active and semi-passive forms of RFID tags contain more hardware than passive RFID tags; and for this reason, the active and semi-passive forms are considerably more expensive to manufacture. Accordingly, the active and semi-passive tags are typically reserved for use with high-cost items wherein a RF signal that can be detected and read over modest distances.

For example, the active and semi-passive tag formats broadcast high frequencies from 850 to 950 MHz that can be detected and read by an external reader located about 100 feet (30.5 meters) away. If it is necessary to read the RF signal emitted by the active and semi-passive tags from greater distances, the inclusion of additional internal batteries can boost a tag's RF signal range to distances well over 300 feet (100 meters).

Also, like many other wireless devices, the active and semi-passive RFID tags broadcast over a large segment or portion of the electromagnetic spectrum. Thus, the chosen exact frequency can be varied as needed or desired; and can be selected to avoid interference with the RF emissions from other electronics, or among several different RFID tags and readers—conventionally known as "tag interference" or "reader interference". Conventional RFID detection systems can also use a cellular system such as Time Division Multiple Access (TDMA) to make sure the wireless communication is handled properly.

In marked contrast, passive RFID transponders rely entirely on the remotely located reader as their sole power source. Consequently in such passive systems, the RFID tag is formed of an antenna and a silicon chip that includes basic modulation circuitry and non-volatile memory. See for example U.S. Pat. Nos. 4,114,151; 5,517,194; 5,153,583; and 6,177,859.

Because passive RFID tags rely entirely on the electromagnetic field generated by the external reader as their sole power source, they are very limited in their broadcast distances. However, passive RFID tags can be effectively used and have their emitted RF signals read up to separation distances of not more than about 20 feet (six meters).

Also, passive RFID tags have substantially lower production costs, commercially meaning that they can be applied for detection of less expensive merchandise. For this reason, passive RFID tags are conventionally manufactured to be disposable tag products, along with the disposable consumer packaging upon which they are typically placed.

Despite these differences, it will be noted and appreciated that all three RFID tag format variants (i.e., active, semi-passive and passive RFID tags) provide very similar operational features and characteristics, which include:

All three variant construct formats are composed of a microchip and an antenna; but only the active and semi-passive formats include an internal battery for power. Typically, a RFID transponder unit contains a semiconductor chip having RF circuits, logic, memory, and an external antenna. The RFID transponder often includes a collection of discrete components—such as capacitors and diodes; a battery in the case of active transponders; a substrate for mounting the components, interconnections between components; and a means of protective physical enclosure. See for example U.S. Pat. Nos. 8,476,689; 8,576,050; 8,587,406; 8,596,544; 8,616,459; 8,628,018; and 8,636,220.

All three variant construct formats are manufactured by mounting the individual elements to a circuit card. This is done by using either short wire bond connections or soldered connections between the board and the circuit elements: chip, capacitors, diodes, antenna. The circuit card may be of epoxy-fiberglass composition or ceramic. The external antennas are generally loops of wire soldered to the circuit card or consist of metal etched or plated on a circuit card. The whole assembly may be enclosed in a plastic box or molded into a volumetric three-dimensional plastic package. See for example U.S. Pat. Nos. 6,147,662 and 6,177,859.

All three variant construct formats have their data stored within a microchip which waits to be electronically read. RFID tags comprise an integrated circuit (IC) attached to an antenna, plus some protective packaging as determined by the application requirements. Specific identification data is stored in the integrated circuit and is sent through the antenna as a responsive or reflected RF signal to a remotely located RF signal reader. See for example U.S. Pat. Nos. 3,967,202; 4,614,945; 4,816,839; 5,528,222; 5,682,143; 5,786,626; 5,825,298; 5,874,902; 5,974,078; 6,104,281; and 8,350,704.

All three variant construct formats require that the remotely located reader pick up the tag's broadcast radio waves and interpret the emitted radiofrequencies as meaningful data. Each RFID transponder unit contains individual coded information which relates to and identifies the object bearing the tag. The remotely located reader of the system sends an initial RF signal over a set distance to the transponder unit. The external antenna of the discrete transponder unit receives the initial RF signal from the remotely located reader; and backscatter modulates the received RF signal with data temporarily or permanently stored in the transponder (such as data indicating the identity and contents of the object to which the transponder is attached). This event, in turn, then produces a sequence of RF response signals in accordance with the transponder's individual code; and this modulated RF response signal is sent back via the external antenna to the remotely located reader. After the RF response signal is received, the remote reader decodes these RF signals to obtain the information and data sent from the transponder unit. See for example U.S. Pat. Nos. 5,641,634; 7,195,149; 7,328,837; 5,892,458; 7,135,977; and 8,587,410.

Unquestionably, RFID transponders are all modestly large articles of manufacture; and as such are intended to be attached to or incorporated into any relatively large object or jumbo sized item—e.g., a bulky or hefty product (suitcases, shipping containers, and kitchen appliances), a living animal maintained as a food source (cattle, pigs, and sheep), or the tangible form of a transportation vehicle (autos, railroad cars, and aircraft). Consequently, there is no such thing as a miniaturized FRID transponder unit; and to date, it has been impossible to make a truly small-sized RFID transponder as such.

For all these reasons, all RFID transponders regardless of type are of-necessity modestly large in both dimensional size and overall volume; and consequently cannot be fitted onto any small-sized area or minimal available surface.

In addition, it has long been recognized that the maximum travel distance over which the RF response signal of the transponder can be broadcast is directly proportional to the power of the available battery and the length of the external antennae. Thus, the RFID response signal broadcast distance is generally very short, and is typically measured in mere meters or feet. As a result, the transponder's RF signal broadcast demands that the included battery be as large as possible, and that the tag's antennae be dimensionally long in size in order to that the broadcast signal travel even a short distance of 30 meters.

Photovoltaic-Cell Powered Transponders

More recently, an entirely different class of miniature electronic transponders have been developed which utilize one or more internal photovoltaic cells to provide electric power for the integrated chip circuitry. The generation of such photovoltaic cell-activated chip transponders concomitantly permits the manufacture of miniature electronic transponder units, which have much smaller dimensions and volume than their predecessor RFID transponders.

For example, a monolithic photovoltaic cell containing electronic transponder unit which includes a transmitting antenna is disclosed by U.S. Patent Publications Nos. 201440048900; 20120325905; 20120318863; 20120241524; and 20120234922 A1—as well as by U.S. Pat. Nos. 5,641,634; 6,590,150; and 7,791,481 respectively

[whose published texts are individually expressly incorporated by reference herein] provides a marked reduction in size and volume for the functional unit.

Other improvements in miniature electronic transponders which utilize photovoltaic cells to provide electric power for the chip circuitry are represented by U.S. Pat. Nos. 7,633,111; 7,098,394; 7,053,294; 7,915,517; 8,089,285; 8,353,917; 8,574,946; 8,552,470; and 8,624,294—whose published texts are individually and collectively expressly incorporated by reference herein.

All such photovoltaic cell-activated chip transponders constitute and operate as a radio frequency identification device wherein electric power is supplied by the conversion of light radiation energy (natural or artificial) into direct electric current using internally placed photovoltaic cells, such as solar cells. In this manner, the photovoltaic cell is used in place of one or more internal batteries; or in place of RF energy harvesting circuits (rectification of the RF signals sent by the remotely located transceiver or reader); or in combination with either or both of these conventionally known sources of energy.

The photovoltaic cell-activated integrated chip transponder is oriented for use with a remotely located interrogator device, reader apparatus, or transceiver unit; and typically comprises a circuit (preferably an integrated circuit) configured to send a responsive signal (containing information to be sent to the reader) in response to an initiating RF signal (either unmodulated or modulated) sent from the remote interrogator/reader/transceiver. A communication antenna is electrically coupled to the transponder's electronic circuitry for wireless RF signal communication with the remotely located interrogator/reader/transceiver. The transponder's emitted response RF signal typically will include specific identification information and related data which is then received and decoded by the interrogator/reader/transceiver.

The photovoltaic cell-activated chip transponder can store any and all information that is deemed to be useful for the particular organization, institution, or business. The encoded data and stored information held within the photovoltaic cell-activated chip transponder can be updated as often as the prevailing conditions change; and subsequent signal communications can keep the human operator apprised of all current or recent changes.

Typically, one or more photovoltaic cells suitable for converting light radiation into electrical energy and providing electrical power to the chip electronic circuit will exist within the dimensional confines of a single transponder unit. A transponder constructed using a photovoltaic cell for operational power can have all the attributes and advantages of a traditional passive transponder unit (i.e., unlimited life, small size, low cost, etc.); with the added advantages of an increased range of communication distance; and may be used for a variety of different high performance applications.

Photovoltaic cell containing transponders also provide major advantages over their predecessor RFID types owing to their operational inactivity in the absence of external light illumination. Thus, if and when desired, a narrowly focused laser light source can and will activate only a single photovoltaic cell transponder unit at a time, even when many other transponders are present within the same use environment. Only the single illuminated photovoltaic cell transponder unit will transmit information and data, while all the other transponder units in the same locale will remain functionally inactive. This capability and reduction in the total number of signal transmitting transponders significantly reduces the background noise level, thereby making the return RF signal easier to detect.

However, if the user wishes the illuminating light to be more broadly applied, any desired total number of photovoltaic cell activated transponders will collectively respond in unison. In this manner, the light energy source can be adjusted to control precisely which individual photovoltaic cell transponders and how many total photovoltaic cell transponder units will be activated and respond on any use occasion.

SUMMARY OF THE INVENTION

The present invention has multiple aspects and alternative definitions. A first aspect is a miniature recognition signal badge suitable for on-demand affixation to and for identifying and sorting among different kinds, shapes and sizes of surgical instruments and tools, said recognition signal badge comprising:

a millimeter-sized three-sheet stack construct which protects against the undesirable effects of impact forces and safeguards its internal contents from degradation by the ambient environment, said millimeter-sized three-sheet stack construct being formed of ($\alpha$) a preformed $1^{st}$ planar sheet composed of opaque matter,
  wherein said $1^{st}$ planar sheet is repellent to water and other aqueous fluids, is resistant to cleaning agents and other noxious chemical compositions, and is enduring of harsh sterilization environments, and
  wherein said $1^{st}$ planar sheet has a predetermined configuration and millimeter-sized dimensions, and presents an anterior face surface and posterior face surface, ($\beta$) a preformed $2^{nd}$ flat sheet composed of dense matter disposed upon and adhered fluid-tight to said anterior face surface of said $1^{st}$ planar sheet,
  wherein said $2^{nd}$ flat sheet is repellent to water and other aqueous fluids, resistant to cleaning agents and other noxious chemical compositions, and enduring of harsh sterilization environments, and
  wherein said $2^{nd}$ flat sheet presents a pre-chosen configuration and millimeter-sized dimensions which are substantially coextensive with the configuration and dimensions of said $1^{st}$ planar sheet, has an anterior face surface and an adhering posterior face surface, and a includes a closed micron-sized aperture space of fixed shape, perimeter edge and volume, ($\gamma$) a preformed $3^{rd}$ level sheet disposed upon and adhered fluid-tight to said anterior face surface of said $2^{nd}$ flat sheet,
  wherein said $3^{rd}$ level sheet is repellent to water and other aqueous fluids, resistant to cleaning agents and other noxious chemical compositions, and enduring of harsh sterilization environments, and
  wherein said $3^{rd}$ level sheet has a pre-chosen configuration and millimeter-sized dimensions not less the dimensions of said $2^{nd}$ flat sheet, and presents an anterior face surface and an posterior face surface, and
  wherein said $3^{rd}$ level sheet is composed entirely of transparent matter which allows on-demand light energy transmissions and presents at least one discernible light energy transmitting zone which is at least co-extensive in surface area with, is aligned to the perimeter edge of, and encloses the cavity volume of said aperture space in said $2^{nd}$ flat sheet;

an operative micron-sized photovoltaic cell-chip transponder unit embedded within and contained by the closed spatial volume of said aperture in said $2^{nd}$ flat sheet of said three-sheet stack construct, said photovoltaic cell-chip transponder unit becoming activated and energized by light energy to generate and electronically emit an identifying RF response signal into the ambient environment; and an adhesive coating disposed on said posterior face surface of said 1st planar sheet of said three-sheet stack construct, said adhesive coating being suitable for on-demand affixation of said three-sheet stack construct and said embedded transponder unit to an exposed surface site of a surgical instrument or tool.

A second aspect provides an operative recognition system suitable for identifying and sorting among different kinds, shapes and sizes of surgical instruments and tools, said system comprising:

a miniature recognition signal badge suitable for on-demand affixation to a surgical instrument or tool and which is comprised of a millimeter-sized three-sheet stack construct which protects against the undesirable effects of impact forces and safeguards its internal contents from degradation by the ambient environment, said millimeter-sized three-sheet stack construct being formed of ($\alpha$) a preformed 1st planar sheet composed of opaque matter,
  wherein said 1st planar sheet is repellent to water and other aqueous fluids, is resistant to cleaning agents and other noxious chemical compositions, and is enduring of harsh sterilization environments, and
  wherein said 1st planar sheet has a predetermined configuration and millimeter-sized dimensions, and presents an anterior face surface and a posterior face surface, ($\beta$) a preformed 2nd flat sheet composed of dense matter disposed upon and adhered fluid-tight to said anterior face surface of said 1st planar sheet,
  wherein said 2nd flat sheet is repellent to water and other aqueous fluids, resistant to cleaning agents and other noxious chemical compositions, and enduring of harsh sterilization environments, and
  wherein said 2nd flat sheet presents a pre-chosen configuration and millimeter-sized dimensions which are substantially coextensive with the configuration and dimensions of said 1st planar sheet, has an anterior face surface and an adhering posterior face surface, and a includes a closed micron-sized aperture space of fixed shape, perimeter edge and volume, ($\gamma$) a preformed 3rd level sheet disposed upon and adhered fluid-tight to said anterior face surface of said 2nd flat sheet,
  wherein said 3rd level sheet is repellent to water and other aqueous fluids, resistant to cleaning agents and other noxious chemical compositions, and enduring of harsh sterilization environments, and
  wherein said 3rd level sheet has a pre-chosen configuration and millimeter-sized dimensions not less the dimensions of said 2nd flat sheet, and presents an anterior face surface and an posterior face surface, and
  wherein said 3rd level sheet is composed at least in part of transparent matter which allows on-demand light energy transmissions and presents at least one discernible light energy transmitting zone which is at least co-extensive in surface area with, is aligned to the perimeter edge of, and encloses the cavity volume of said aperture space in said 2nd flat sheet, an operative micron-sized photovoltaic cell-chip transponder unit embedded within and contained by the closed spatial volume of said aperture in said 2nd flat sheet of said three-sheet stack construct, said photovoltaic cell-chip transponder unit becoming activated and energized by light energy to generate and electronically emit an identifying RF response signal into the ambient environment, and an adhesive coating disposed on said posterior face surface of said 1st planar sheet of said three-sheet stack construct, said adhesive coating being suitable for on-demand affixation of said three-sheet stack construct and said embedded transponder unit to an exposed surface site of a surgical instrument or tool;

a source of light energy whose light transmissions can be directed to said 3rd sheet of said miniature recognition signal badge; and a RF signal ID reader operative for detecting and reading responsive identifying RF signals sent from said embedded micron-sized photovoltaic cell-chip transponder unit of said miniature recognition signal badge.

BRIEF DESCRIPTION OF THE DRAWING

The present invention may be more easily understood and better appreciated when taken in conjunction with the accompanying Drawing, in which:

Prior Art FIG. 1 shows the conventional "anatomy" of hand-held surgical instruments and tools;

Prior Art FIG. 2 shows alternative examples of hemostats such as the Mosquito, Kelly, Carmalt, Schnidt tonsil, and Kocher types;

Prior Art FIG. 3 shows alternative examples of haemostatic forceps such as the Backhaus Towel, Allis Intestinal, Babcock Intestinal, Kocher Artery, Mixter Gall Duct, Kantorwitz Right Angle, and Forester varieties;

Prior Art FIG. 4 shows alternative examples of thumb forceps such as the Adson, Brown-Adson, Hudson, Dressing, Tissue Forceps with Teeth, Russian, Cushing, and DeBakey varieties;

Prior Art FIG. 5 shows alternative examples of needle holders such as the Mayo-Heagar, Crile-Wood, Olsen-Hegar, Collier, Webster, and Castroviejo kinds;

Prior Art FIG. 6 shows alternative examples of different scissors types such as the Mayo Dissecting Straight, Mayo Dissecting Curved, Metzenbaum, Metzenbaum Delicate, Potts-Smith, Lister Bandage, Iris Straight, and Stevens Tenotomy scissors;

Prior Art FIG. 7 shows alternative examples of different retractors such as the Richardson—Eastman, Mayo, Jansen Mastoid, Weitlaner, Cerebellum, Gelpi, Volkman Rake, Green Goiter, Army-Navy, and Deaver retractors;

Prior Art FIG. 8 shows alternative examples of different probes and knife handles;

Prior Art FIG. 9 shows a typical alignment of string instruments on a tray as a set collection;

Prior Art FIG. 10 shows the manner of proper instrument placement in a tray;

FIG. 11 is an overhead view of an exemplary minimalist embodiment of the present invention, a recognition signal badge;

FIG. 12 is a cross-sectional view of the exemplary minimalist embodiment for the recognition signal badge shown by FIG. 11;

FIGS. 13A-13F respectively illustrate the simplest, non-commercial, and least complicated procedure for making an operational and functional recognition signal badge;

FIG. 15 is an overhead view of a commercially preferred and best mode embodiment of the recognition signal badge;

FIG. 16 is a cross-sectional view of the commercially preferred and best mode embodiment of the recognition signal badge shown by FIG. 15;

FIGS. 18A-18K respectively illustrate the series of manipulative steps for making a preferred embodiment and commercially desirable recognition signal badge.

DETAILED DESCRIPTION OF THE INVENTION

Figure 13F:
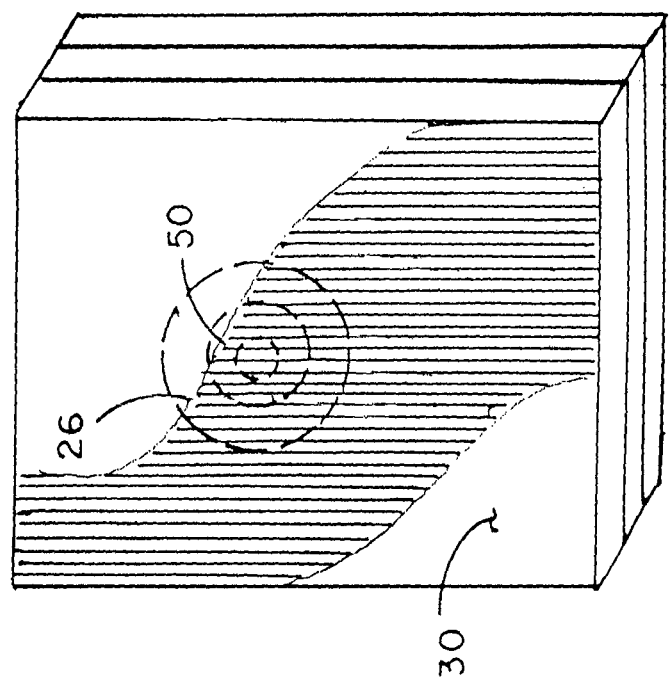

The present invention is a discrete signal-emitting badge and operative system for recognizing, differentiating and distinguishing among the many kinds, shapes and sizes of surgical instruments and tools commonly used today for human and veterinary surgeries. The signal-emitting badge is a discrete millimeter-sized article of manufacture which can be easily affixed to an exposed surface of any type, any configuration and any dimension of surgical instrument or tool; and includes a well-cushioned and protected photovoltaic cell-integrated chip transponder unit embedded within a safeguarding three-tier stack construct. The photovoltaic cell of the embedded transponder is activated by the introduction of light energy in any form; and once activated, provides electric power to the electronic circuitry of the transponder unit of the instrument-affixed badge such that a responsive identifying RF signal is emitted to the ambient atmosphere. That emitted responsive identifying RF signal is detected and decoded by a remotely located reader; and then translated into readable form on a display for human visualization and acknowledgement.

I. The Unappreciated True Challenges Confronted and Solved by the Present Invention In order to appreciate better what are the unique structural features and functional advantages of the present invention as a whole, one must see the nature of the true problem from the perspective and frame of reference of the ordinarily skilled designer of conventional identification systems when faced with the problem of properly identifying hand-held surgical instruments and tools. There are a number of serious and substantive challenges which must be individually confronted and solved. All of these are manifest and weighty problems; and each of them must be effectively addressed and solved. In addition, the entire set of challenges must be collectively and cumulatively dealt with successfully and answered in decisive terms concurrently. Consequently, what might to the unacquainted seem to be merely superficial, or cosmetic, or cursory features—upon subsequent reflection and deliberation instead reveals itself to be markedly substantive, highly significant, and truly meaningful.

The true perspectives and proper frame of reference concerning these major challenges therefore are all of the following:

(a) A first decisive challenge is how does one construct a millimeter-sized recognition signal badge containing an embedded CMOS-chip transponder unit as a discrete and operative article of manufacture which is responsive to a pre-chosen activation signal and energy source sent by a remotely located transceiver. It is imperative that the problem of miniature sizing for the recognition signal badge as a discrete article be solved completely and satisfactorily.

(b) A second serious difficulty is how does one physically attach a millimeter-sized recognition signal badge (which includes an embedded CMOS-chip transponder as an operative component) onto a small exposed surface area of a surgical instrument or tool in a precisely oriented and reliable manner. The complete recognition signal badge is a discrete article which must become sufficiently joined and affixed to a limited surface area of the tangible object such that its juncture to that particular location continues over and endures for at least several calendar years' time.

(c) A third prominent burden is how does one provide for sufficient resistance to impact (compression) forces for the affixed recognition signal badge containing an embedded CMOS-chip transponder unit such that the electronic circuitry remains functional and operational indefinitely while the surgical instrument or tool is used for its intended purpose. A true solution to this impact force problem must take into account the fact that the CMOS chip of the transponder unit is made of silica, a very brittle material which is subject to breaking and fragmenting upon impact or collision with another hard surface—an event which often occurs with surgical instruments loosely arranged and having free movement within a surgical instrument tray. In addition, the CMOS chip of the embedded transponder within the affixed badge must somehow be protected and be made resistant to breaking if and when the surgical instrument or tool is rolled on or otherwise encounters a hard surface, such as a table; or is accidentally dropped on the floor by the surgeon during use in the surgical procedure.

(d) A fourth noteworthy challenge is the available exposed surface area then existing on the individual instrument or tool which can properly serve as an affixation site for a millimeter-sized recognition signal badge (which includes a discrete CMOS-chip transponder as an operative component). This particular challenge presents two notably different, but intimately related, sub-problems—which are:

To be both operative and effective, there must exist an unobstructed and optically clear travel direction pathway for an activation signal to reach the embedded CMOS-chip after the badge is physically affixed to the instrument surface. This unhampered travel direction pathway requirement exists and signifies that any pre-chosen type of activation signal and energy source (such as laser light energy) sent by a remote transceiver device must not only have unhampered access to and an open path for directly reaching the embedded CMOS-chip of the transponder unit; but also present sufficient signal strength and energy power at the moment of direct contact to activate the CMOS-chip and allow the then energized chip to respond and broadcast its unique recognition-return signal to a remotely placed reception device.

The mode of attachment for the discrete badge to small radii instrument surfaces itself must avoid unintentional creation of obstructions and avert accidental blockage of an available clear optical pathway to the embedded CMOS-chip. Thus, the affixation technique for the badge cannot allow use of any dense adhesive label which might be wound over itself, thereby unintentionally covering the embedded CMOS-chip, and consequently not allowing the CMOS-chip to receive sufficient activation signal and/or energy power to activate or to broadcast a response signal in sufficient strength and adequate distance for the remote receiving device to record it.

(e) A fifth crucial challenge is how does one adequately protect a recognition signal badge (containing an embedded CMOS-chip transponder unit) which has been affixed to a particular surgical instrument or tool from the extremely harsh treatments and process conditions caused by repeated sterilization processing. It is unquestionable that proper sterilization of each surgical instrument and tool must occur before that item can be used for human or veterinary surgery. Sterilization is conventionally performed using dry high heat, or via pressurized steam, or by gas exposure, or with gamma light irradiation. Thus it must be appreciated that each time a surgical instrument or tool is sterilized, the affixed recognition signal badge and its embedded CMOS-chip also become subjected to these germ-destroying processes; and if the embedded CMOS-chip is not sufficiently protected, its electronic circuitry will cease to function.

II. A Minimalist Embodiment of the Recognition Signal Badge Precise Nomenclature & Terminology For greater clarity of description and ease of proper understanding, it is essential that the nomenclature, terminology, structural orientations, and functional features of the present invention be presented in unambiguous and precise terms, wording and phrasing. For these purposes, each discrete item, entity, and moiety employed for or existing within any embodiment of the recognition signal badge as a functional article of manufacture will be described by consistently employing only the following terminology:

The anterior face surface of any single sheet of material is primarily termed the "obverse" side; and its acceptable alternative terms include "front", "principal", "upper", "forward", and "dominant".

The posterior face surface of any single sheet of material is primarily termed the "reverse" side; and its acceptable alternative terms include "rear surface", "back surface", "underside", "opposite side", "contrary side", and "counterpart".

The interim product of combining any two discrete sheets of material together as a co-joined unit is primarily termed an "aggregate"; and its acceptable alternative terms include "two-tier mass", "dual pile", "pairing", "tandem", "matched set", "couplet", and "brace".

The result of joining three discrete sheets of material together as a single collective entity is primarily termed a "stack"; and its acceptable alternative terms include "triplet", "trio", "assemblage", "laminate", and "three-tiered composite".

The three-tiered stack construct containing an embedded photovoltaic cell-integrated chip transponder unit existing as a complete and operative article of manufacture is primarily termed a "badge"; and its acceptable alternative terms include "emblem", "medallion", "marker", "sticker", and "tab".

The Illustrated Minimalist Embodiment

A exemplary minimalist embodiment of the recognition signal badge is illustrated by FIGS. 11 and 12 respectively. As shown therein, a tiny recognition signal badge is shown in overhead and cross-sectional views as a miniature article of manufacture which serves to differentiate and distinguish among different kinds, shapes and sizes of surgical instruments and tools. The minimalist badge contains a functionally complete and internally embedded photovoltaic cell-integrated chip transponder unit—which can be encoded at will to generate and to emit a singular identifying RF response signal on-demand; and can be affixed on-demand to an exposed surface and pre-chosen site of a single kind, shape and size of surgical instrument or tool whose unique individual characteristics have been correlated with only that particular identifying RF response signal.

The Three-Tiered Stack Construct of the Recognition Signal Badge

As illustrated by FIGS. 11 and 12 respectively, the tiny recognition signal badge 2 is a discrete millimeter-sized article of manufacture having a protective three-tiered stack structure, which is constructed as follows:

(i) A first planar sheet and preformed base layer 10 composed of at least one type of opaque matter which is repellent to water and other aqueous fluids, is resistant to cleaning agents and other noxious chemical compositions, and is enduring of harsh sterilization environments. The preformed base layer 10 in this illustrated minimal embodiment has a substantially square overall configuration; has about a 2 millimeter (mm) sized length and width dimension totaling about 4 mm square in area; and presents a uniform thickness dimension typically ranging from about 4-10 mils (101.6-254.0 microns). This first base sheet also presents an anterior face surface 12 as the obverse side and a posterior face surface 14 as the reverse side of the base layer. Both the obverse side 12 and the reverse side 14 of this first sheet 10 have particular functions and application.

(ii) A second flat sheet and preformed intermediate layer 20 is composed of at least one type of dense matter which is repellent to water and other aqueous fluids, is resistant to cleaning agents and other noxious chemical compositions, and is enduring of harsh sterilization environments. The preformed second flat sheet 20 presents a discrete anterior face surface 22 as the obverse side and an adhering posterior face surface 24 as the reverse side of the intermediate layer; and the discrete sheet 20 is aligned with, is disposed upon, and is permanently adhered in a fluid-tight manner to the anterior face surface 12 of the first planar sheet 10.

Typically, this second flat sheet 20 is a preformed intermediate layer which has a similar configuration and presents millimeter-sized length and width dimensions which are substantially coextensive with the generally square configuration and 2 millimeter sized length and width dimensions of the first planar sheet 10 (and thus also total about 4 mm square in area). The illustrated second sheet 20 also has a uniform thickness dimension ranging from about 4-6 mils (101.6-152.4 microns).

In addition, the preformed second sheet 20 will always include and invariably present a discernible micron-sized aperture space 26 of fixed shape, perimeter edge and cavity volume. As illustrated by FIGS. 11 and 12, the micron-sized aperture space 26 appears as a round or circular shaped, die-cut opening or hole. However, this circular aperture configuration is merely one of many different shape possibilities; and this rounded spatial format is employed in this illustrated minimalist embodiment merely as a convenience.

Thus, without regard to its true configuration, the dimensions and depth of the aperture space 26 will always be limited to be a micron-sized cavity and void volume. Accordingly, the approximate diameter of the illustrated round aperture space 26 will typically range from less than 1,000 microns to about 300 microns; and the depth of the spatial cavity will frequently be only about 4-6 mills (101.6-152.4 microns) in size.

(iii) A third level sheet and preformed top layer 30 is composed (at least in major part) of a clear material or transparent substance which is repellent to water and other aqueous fluids, is resistant to cleaning agents and other noxious chemical compositions, and is enduring of harsh sterilization environments. The preformed third level sheet 30 presents a discrete anterior face surface 32 as the obverse side and an adhering posterior face surface 34 as the reverse side; and is aligned with, is disposed upon, and is permanently adhered in a fluid-tight manner to the anterior face surface 22 of the second flat sheet 20.

Accordingly, the third level sheet 30 will have a configuration and millimeter-sized length and width dimensions which are never less the actual length and width dimensions of the second intermediate layer 20—and thus in this minimalist embodiment also are each about 2 mm and total about 4 mm square in area; and present a thickness or depth dimension, which in this illustrated minimalist embodiment is only about 4-6 mills (101.6-152.4 microns) in size—but optionally can vary from about 4-15 mills in thickness in alternative embodiments, if and when so desired.

Accordingly, this third sheet is longer and extends bilaterally from the first two sheets. It can be cut, however, to size such that this third sheet can be wound 1.5 times around the circumference of a round handle or aperture; and for very tiny instruments, this sheet can be wound twice around the girth of the tiny instrument.

Requisite Structural Features and Beneficial Functions of the Discrete Sheets

It will be noted and appreciated that the $1^{st}$ planar sheet 10 and the $2^{nd}$ flat sheet 20 and the $3^{rd}$ level sheet 30 must individually provide and demonstrate a variety of different requisite structural features and functions in the three-tiered stack construct, which are:

(1) Initially, the anterior face surface 12 of the discrete $1^{st}$ sheet 10 acts and serves to cover and enclose the bottom aspect of the aperture space 26 as a concomitant act during the event of the $1^{st}$ sheet 10 becoming adhered and permanently joined to the discrete $2^{nd}$ sheet 20. As the two-ply aggregate is formed via adherence of the 1st and $2^{nd}$ sheets together, the concomitant act of the anterior face surface 12 covering and enclosing the bottom end of the aperture space 26 invariably occurs. Consequently, the aggregate of the 1st and $2^{nd}$ sheets joined in combination will always reveal a closed bottom end for the existing aperture space 26.

(2) The placement and adherence of the discrete $3^{rd}$ top sheet 30 upon the anterior face surface 22 of the second flat sheet 20 also concomitantly causes an invariable covering and enclosure of the upper aspect of the aperture space 26 in the second flat sheet 20. Given that the three-tiered stack structure 106 is formed via such juncture, the placement of the $3^{rd}$ discrete sheet upon the $2^{nd}$ sheet 20 concomitantly and invariably acts to cover and enclose the upper end of the aperture space 26. Thus, as the $3^{rd}$ sheet is adhered to the anterior face surface 22, the cavity volume of the aperture space becomes fully closed, self-contained, and sealed fluid-tight. Thus, any tangible item (such as an operative transponder unit) which is then disposed and rests within the limited cavity volume of the aperture space 26 concurrently becomes encapsulated and completely contained within the sealed aperture's dimensional confines.

(3) The 3rd level sheet and top layer 30 must always provide at least one discernible zone of clear matter or transparent material which allows for both unhindered light energy transmissions and unobstructed responsive RF signal passage on-demand. Thus, the third sheet 30 always will present and include at least one discernible light energy transmitting zone whose transparent fixed surface area and perimeter edges are aligned with and are at least co-extensive in size with the particular configuration and dimensions of the aperture space 26 in the second flat sheet 20. In each and every embodiment, it is through this definitive light transmitting zone and fixed transparent surface area that light energy signals will travel unhampered and responsive RF signals will freely pass.

Nevertheless, it will be noted and appreciated that in the illustrated minimalist embodiment shown by FIGS. 11 and 12, the entirety of the third level sheet 30 is composed of a transparent substance which allows free and unhindered light energy signal passage. Consequently in this minimalist instance (as well as in the majority of alternative embodiments), the whole clear substance and transparent layer of the preformed top sheet 30 is itself the discernible light energy signal transmitting zone; and via this mode of whole sheet transparency, the rounded configuration and diameter dimension of the aperture space 26 in the second flat sheet 20 is properly covered and enclosed by material allowing unhampered transmission of light energy signals into the cavity volume of the aperture space 26 and free passage of responsive RF signals emanating from the aperture space 26.

(4) It is required that each discrete sheet—i.e., the preformed $1^{st}$ base sheet and the preformed $2^{nd}$ intermediate sheet and the preformed $3^{rd}$ top sheet—forming the three-tier composite become firmly attached and permanently joined in a fluid-tight manner to its adjacent neighbor layer. The fluid-tight juncture and permanent bonding of these three individual sheets together yields a single multi-ply stack which is protective and safeguarding against external impact forces and collision effects; is repeatedly able to repel water and other aqueous fluids; is highly resistant to cleaning agents and noxious chemical compositions; will repetiously endure and withstand the extremely harsh treatment conditions of repeated sterilization (via any conventionally known method); and can last for a long-term period of usage extending several calendar years in duration.

The fluid-tight juncture and bonding of these preformed sheets together into a single unified composite arrangement preferably employs high-strength, temperature resistant, and long lasting adhesive substances for this purpose. There are today many different conventionally known and commercially available adhesive compounds and bonding compositions that are heat and moisture resistant, that are high temperature durable, and which can effect permanent bonding of multiple discrete layers. All such adhesives and bonding agents are typically applied as a distinct coating to each posterior face surface of each discrete sheet before joining the sheets together in the making of a three-tiered stack construct.

(5) Another major benefit of the badge construct is that the three-tier structure shields the embedded transponder unit from the effects of any electrical current in the surgical instrument or at an attached surface. For example, surgeons will sometimes cauterize tissue by clamping the tissue in a cavity, and then touch the cautery to the instrument—thereby cauterizing the tissue where the instrument is clamped. The stacked construct of the badge arrangement protects and shields the embedded transponder unit while the cauterization procedure is being performed.

Capabilities of the Three-Tiered Composite

Accordingly, in the illustrated minimalist embodiment (as well as for any other alternative embodiment of the invention as a whole), the discrete three-tiered stack construct will routinely provide and consistently present a range and variety of desirable structural characteristics and properties, which include each of the following:

The triple layer structural integrity of the constructed three-tier stack arrangement will remain resilient, materially uniform and dimensionally unaltered over its entire lifetime of intended and expected usage.

The $2^{nd}$ sheet and intermediate layer of the three-tier stack will consistently and invariably present and provide a micron-sized aperture space of set configuration, determinable dimensions, and measurable cavity volume.

The triplet structure of the three-tier stack is and will remain reliably impervious to water and other aqueous fluids; will be tolerant of and resistant to repeated treatment with strong cleaning agents and noxious chemical compositions; and will be lasting against and enduring of repetitious harsh sterilization processing.

The triplet construction of the three-tier stack will adequately protect and long safeguard the photovoltaic cell-activated transponder unit embedded within the construct from major impact forces and the damaging effects of inadvertent collisions with surrounding tangible objects.

The triplet construction of the three-tier stack will adequately protect and long safeguard the photovoltaic cell-activated transponder unit embedded within the construct from the effects of any electrical current in the surgical instrument or at an attached surface.

The laminated assemblage of the three-tier composite will consistently allow light energy signals—i.e., any form, frequency or intensity of light radiation existing as either particles or waves—to pass freely and unhampered through its transparent top layer, and then to enter the micron-sized cavity volume of the configured aperture space within the $2^{nd}$ intermediate layer of the three-tier stack arrangement.

The unitary three-tier composite will on any and all occasions allow radiofrequency (RF) waves and signals generated by a photovoltaic cell-activated transponder unit (then embedded within the confines of the micron-sized volume of the configured aperture space within the $2^{nd}$ intermediate layer of the stack arrangement) to travel outwardly, and pass freely through the transparent top sheet of the three-tiered stack, and ultimately be released into the surrounding air environment.

The Photovoltaic Cell-Integrated Chip Transponder Unit

Within the discrete millimeter-sized three-tiered stack construct 6 resides an operative micron-sized photovoltaic cell-integrated chip transponder unit 50. This transponder unit 50 lies embedded within and is completely contained by the enclosed micron-sized cavity volume of the aperture space 26 then existing within the material substance of the intermediate sheet 20.

The embedded photovoltaic cell-integrated chip transponder unit 50 can be activated on-demand, and will become energized by light energy signals passing through the top transparent sheet 30 of the stack construct 6. After receiving and converting such a light energy transmission, the embedded transponder unit will produce and electronically emit an encoded identification RF response signal—which then travels through the material thickness of the transparent third top sheet 30 into the and immediately surrounding environment, and can be detected by a remotely located reader/detector apparatus.

Operationally, each micron-sized photovoltaic cell-integrated chip transponder unit will contain individual encoded information or data which relates to and identifies the object bearing the affixed recognition signal badge. The remotely located transceiver of the identification system sends an initial light energy signal (e.g., laser light of a pre-chosen frequency and intensity) over a short distance (several meters) to the micron-sized photovoltaic cell-integrated chip transponder unit embedded within the affixed recognition badge. The photovoltaic cell of the embedded transponder unit receives and accepts the initial light energy signal from the remotely located transceiver; and converts the received light energy signal into internal electric current power for the chip circuitry, which then holds coded data indicating the identity of the object to which the recognition badge is attached. The chip circuitry, in turn, then produces and emits a response RF signal(s) corresponding to the transponder's individual coded identity data; and this emitted response RF signal is sent back over a limited distance to the remotely located reader/transceiver.

After the response RF signal(s) is detected and received, the remotely located reader/transceiver decodes the response RF signal(s) and then typically displays the decoded information sent from the micron-sized photovoltaic cell-integrated chip transponder unit to the surgical technician.

As previously described herein concerning CMOS technology as a whole, a photovoltaic cell powered-integrated circuit transponder typically comprises a silica wafer semiconductor chip with internal circuitry sufficient to broadcast a unique identifying number or data; but is a miniature-sized transponder unit which does not employ either a battery or a large-sized antennae. In this particular kind of CMOS technology, the transponder's internal circuitry employs one or more tiny photocells which accept and absorb light energy rays (transmitted from a remotely located external light source) in order to activate and electrically power the chip's circuitry. The transponder also includes a very small signal-transmitting antenna by which a responsive RF signal broadcast is sent into the ambient environment for detection and acceptance by a remotely located reader/transceiver.

The entire photovoltaic cell—integrated circuit transponder unit embedded in the spatial volume of the aperture of the second flat sheet is now miniscule in scale and size; and is at most about 500 microns square in area, and typically is no more than about 100 microns in thickness or depth. Such micron-sized transponders with photovoltaic cell activated integrated circuitry are presently commercially manufactured and sold as the P-Chip® transponder [Pharmaseq Inc., Princeton N.J.].

The heart of the micron-sized photovoltaic cell-integrated chip transponder is an ultra-small light-powered electronic chip circuitry electrically joined to an antenna. The chip is a monolithic integrated electrical circuit made using standard/conventional manufacturing technology. An essential part of the P-Chip® transponder unit is its internal photovoltaic cell, which when illuminated by light energy, is activated and provides adequate electric power for operating the electronic circuits of the chip. The remaining electronic circuitry of the P-Chip® silicon wafer are typically a read-only memory unit for the unique 50-bit ID decoders and counters; and a small simple radio antenna for transmission of a return RF signal.

Moreover, there are commercially available at least two different micron-sized constructed versions of a completely functional and operative P-Chip® transponder: A 500×500× 100 micron sized unit and a 250×250×50 micron sized unit respectively.

In addition, a portable RF signal ID reader is also commercially available from the manufacturer [Pharmaseq Inc., Princeton N.J.]; and such an remotely located response-signal ID reader/detector can and will communicate with any personal computer (PC) system via a standard USB port. The Series 8000 PharmaSeq Wand is both suitable and operative for detecting and reading responsive RF signals sent from embedded P-Chip® transponders. This response-signal ID reader/detector is calibrated for object identification applications; and includes CD-ROM with p-Chip Reader Software (compatible with Microsoft Excel, Access, and similar software programs).

On-Demand Affixation Means

Lastly, the discrete millimeter-sized three-tiered composite 6 will typically also include on-demand affixation means—i.e., an adhesive substance which typically will appear as a discrete coating and lie disposed over the posterior face surface 14 of the first base sheet 10 in the three-sheet stack construct; and a peel away liner joined to the adhesive coating is commonly used to expose the adhesive for affixation to a pre-chosen surface. Thus, given an adhesive substance disposed as a discrete coating upon the posterior face surface (rearward side) of the $1^{st}$ planar sheet and base layer of the three-sheet stack construct—the complete recognition signal badge can become subsequently affixed at will to any chosen surface of a surgical instrument or tool.

For these reasons, the adhesive substances suitable for achieving the co-juncture and bonding of the three sheets together into a unitary triplet article, as well as the adhesives to be used for subsequent affixation of the recognition signal badge to another object, should be carefully chosen in advance to provide particular chemical and physical properties that meet all the unique and singular challenges described in detail above.

III. Making a Minimalist Embodiment of a Recognition Signal Badge

For ease of understanding, the simplest and least complicated procedure for making an operational and functional recognition signal badge is shown by FIGS. 13A-13F respectively. It will be noted and appreciated, however, that this very simple manner of manufacture is not deemed to be a commercially viable process. Nevertheless, the simplest procedure is deemed to be the best teaching of what is effectively required.

Initially, FIG. 13A shows an elevated view of the $1^{st}$ planar sheet 10 as a preformed square-shaped base layer having an anterior face surface 12 and a posterior face surface, with an adhesive and backed with a peel away liner (not visible in the illustration). Similarly, FIG. 13B shows elevated view of the $2^{nd}$ flat sheet 20 as a preformed square-shaped base layer having an anterior face surface 22; a posterior face surface 24 (not visible in the illustration); and a micron-sized aperture 26 of fixed shape, perimeter and spatial volume. The posterior surface of the $2^{nd}$ flat sheet 20 has been previously coated with a pre-chosen adhesive 27, a bonding agent which will form a strong and permanent fluid-tight union with another object on-demand.

Step 1 of the manufacturing process begins when the preformed $2^{nd}$ intermediate sheet 20 is aligned with and physically placed upon the anterior face surface 12 of the $1^{st}$ planar sheet 10. The result of this juncture and bonding is a two-ply aggregate 40, as shown by FIG. 13C.

Step 2 of the process is the placement of an operative micron-sized photovoltaic cell-integrated chip transponder unit 50 into the micron-sized aperture space 26 of the $2^{nd}$ flat sheet 20. This placement event is shown by FIG. 13D.

FIG. 13E shows an elevated view of a $3^{rd}$ level sheet 30 as a preformed square-shaped and completely transparent top layer having an anterior face surface 32 and a posterior face surface (not visible in the illustration). The posterior surface of the $3^{rd}$ level sheet 30 also has been previously coated with a pre-chosen adhesive 37, a bonding agent which will form a strong and permanent fluid-tight union with another object on-demand.

Step 3 of the manufacturing process begins when the preformed transparent top sheet 30 is aligned with and physically placed upon the anterior face surface 22 of the $2^{nd}$ intermediate sheet 20. The result of this juncture and bonding is a three-tier stack construct 6 having an embedded micron-sized photovoltaic cell-integrated chip transponder unit 50, as is shown by FIG. 13F.

Lastly, although not formally part of the complete recognition signal badge construction—but rather as a matter of both convenience and practical reality—it is very desirable that a suitable adhesive composition be disposed as a discrete coating on the posterior face surface (rearward side) of the $1^{st}$ base sheet of the three-sheet stack construct. Furthermore, in order that the complete recognition signal badge will become properly affixed to only a pre-selected site and surface of a surgical instrument or tool on-demand, a conventional peel-away backing sticker [not shown] is then overlaid upon the adhesive coating then disposed upon the posterior face surface (rearward side) of the $1^{st}$ base sheet.

It is intended that a human operator will remove this peel-away backing liner immediately in the conventional manner before placing the adhesive-coated posterior face surface of the $1^{st}$ base sheet in the three-sheet stack construct upon the pre-selected site and surface of a surgical instrument or tool.

IV. Differences and Variances Among the Three Discrete Sheets in the Stack Construction of a Recognition Signal Badge

Major Differences Among the Three Individual Sheets

As a structured article of manufacture, the recognition signal badge of the invention exists as a three-sheet stack construct which is overtly limited in its length and width dimensions, and is severely restricted in its depth (or thickness) dimension to only a few mils. By scientific definition, a "millimeter" is a unit of dimension equal to $1\times10^{-6}$ meters; and a "mil" is a unit of dimension equal to $1/1000$ inches, or 0.0254 millimeters, or 25.4 microns.

Although appearing as discrete layers and strata in the three-sheet stack construction of the recognition signal badge, there are nevertheless a wide range substantive differences existing among the individual strata based upon their particular positioning in the three-tiered arrangement and organization. A useful summary of such structural differences and organizational distinctions is presented by Table 1 below.

TABLE 1

Major Differences By Sheet Position

| Moiety | Stratum Type | Location | Primary Function | Kind of Material | Major Attribute |
|---|---|---|---|---|---|
| $1^{st}$ layer | base | bottom | impact force absorbance | opaque | support |
| $2^{nd}$ layer | intermediate | middle | aperture holding frame | dense | transponder containment |
| $3^{rd}$ layer | exterior | top | protection & shielding | transparent | light energy transmission |

Permitted Variances in the Configuration of the Individual Sheets and the Badge Shape as a Whole In general, it is most desirable, although not compulsory, that the configuration of each individual sheet in the three-tiered stack arrangement be similar, if not identical. In the minimalist square-shaped embodiment of the recognition signal badge shown by FIGS. 11 and 12 respectively, the $1^{st}$ base sheet and the 2$^{nd}$ intermediate sheet and the 3$^{rd}$ top sheet are exactly alike in overall square shape.

Figure 14:
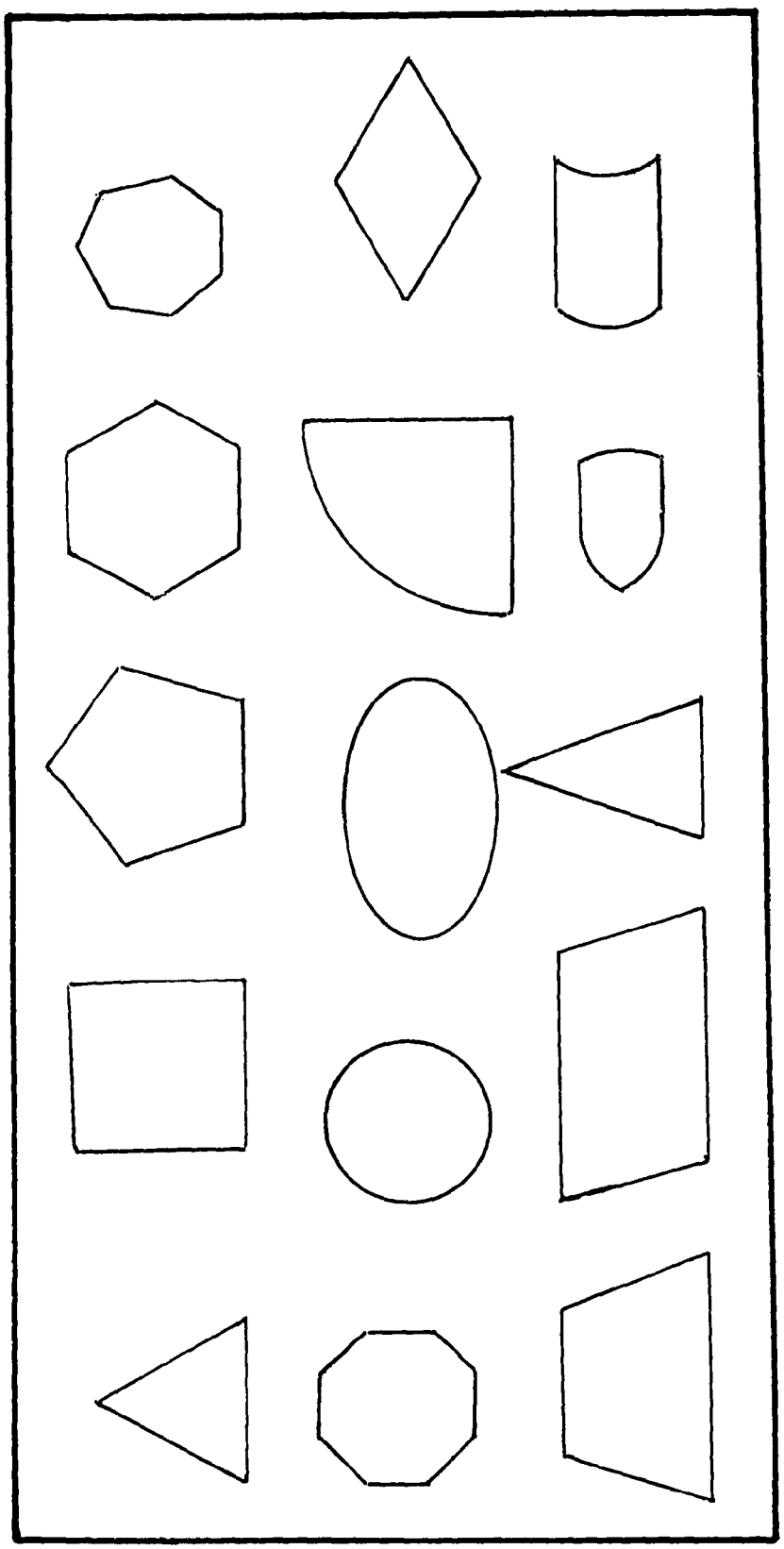
FIG. 14 illustrates the range and variety of alternative sheet configurations available to the manufacturer when making a recognition signal badge.

However, there is no necessity or requirement as such that only a square configuration be utilized. To the contrary, it is intended and expected that a large and diverse variety of alternative sheet configurations can and will be used in order to meet and satisfy different badge affixation circumstances. Accordingly, as merely representative and exemplary of the many different sheet configurations available to the manufacturer of the recognition signal badge, the alternative sheet shapes and forms shown by FIG. 14 are offered.

In addition, there is no necessity that the chosen sheet configuration be a recognized geometric form; nor need the selected sheet shape be either regular, or uniform, or symmetrical, or non-skewed as such. To the contrary, any sheet design is acceptable so long as there is a set perimeter edge and measurable surface area for the individual stratum.

Permitted Variances in the Length and Width Dimensions of the Individual Sheets

As illustrated by FIGS. 11 and 12 respectively, a minimalist embodiment of the recognition signal badge typically utilizes similar, if not identical, length and width dimensions for each individual sheet in the three-tiered stack arrangement. Thus, the illustrated minimal embodiment utilizes a 1$^{st}$ base sheet, and a 2$^{nd}$ intermediate sheet, and a 3$^{rd}$ top sheet which are each about 2 mm in length, about 2 mm in width, and about 4-6 mils in depth (thickness).

However, while keeping in mind that the entire construction should be as small in millimeter size as reasonably possible, a meaningful range of different dimensional sizes for each individual sheet in the three-tiered stack are nevertheless available to the manufacturer. Thus, the range of length dimensions for the 1$^{st}$ base sheet can vary from about 0.1.0 mm-12.0 mm; and the range of length dimensions for the 2$^{nd}$ intermediate sheet can also vary from about 1.0 mm-12.0 mm; while the range of length dimensions for the 3$^{rd}$ top sheet can vary far more and be from about 1.0 mm-200.0 mm in size.

In a similar manner, the range of width dimensions for the 1$^{st}$ base sheet can vary from about 1.0 mm-12.0 mm; and the range of width dimensions for the 2$^{nd}$ intermediate sheet can also vary from about 1.0 mm-12.0 mm; while the range of width dimensions for the 3$^{rd}$ top sheet is variable in size from about 1.0 mm-15.0 mm.

The range of variances for the depth or thickness dimension for each discrete sheet is discussed below.

Permitted Variances of the Individual Sheet's Thickness Dimension

Given the minimalist embodiment described above and illustrated by FIGS. 11 and 12 herein, it is frequently desirable that each discrete sheet in the three layer stack construction of the recognition badge be varied in its thickness dimension. Accordingly, each individual layer of the three-sheet construct be will described individually.

The 1$^{st}$ sheet and base layer of the stack should typically be standardized in its thickness or height dimension to the minimal 3-4 mil size. It will be noted that the 1$^{st}$ sheet of the three-tier stack not only serves as the support stratum for juncture with the other two discrete sheets, but also functions in reality as an impact force resistance base layer which can accept and absorb shock waves and collision forces for the entire badge structure as a whole; and also shields the embedded transponder unit from the effects of electrical current.

Thus, it is generally desirable that the thickness dimension of the base layer preferably be kept at 3-5 mils (0.1524-0.2032 millimeters) in size; but optionally can be as much as 10-12 mils (0.2540-0.3048 millimeters) in size.

The 2$^{nd}$ sheet and intermediate layer of the three-tiered laminated construction should be strictly controlled in its thickness or height dimension in order to minimize its available aperture depth. From the description presented above for the minimalist embodiment, it is clear that the intermediate layer's purpose and function is two-fold in nature.

First, the discrete 2$^{nd}$ sheet must provide an aperture space which will hold and contain the entirety of the micron-sized photovoltaic cell-integrated chip transponder unit within its cavity volume. Consequently, the shape and cavity volume of the aperture must provide sufficient encapsulating space to accommodate the true dimensions and overall girth of the transponder unit without causing undue physical contact.

Second, this intermediate layer must restrain the encapsulated micron-sized photovoltaic cell-integrated chip transponder unit from unwanted free movement while resting within the sealed cavity volume of the aperture space. This second function deserves some further explanation in order to be properly understood.

It will be remembered that the embedded transponder unit contains not only a photovoltaic cell (for conversion of received light energy signals into electrical current); but also includes an electronic integrated chip (IC) made of silica—a very brittle material which is subject to breaking and fragmenting upon impact or collision with a hard object such as a table surface or a surgical instrument. Precisely because it is inevitable impact force contacts and collisions with hard objects must occur repeatedly over time while the recognition signal badge is affixed to a particular instrument or tool, it therefore becomes both critical and essential that disposed micron-sized photovoltaic cell-integrated chip transponder unit then lying within the spatial confines of the aperture in the 2$^{nd}$ intermediate sheet be restrained and curtailed as much as possible from free sliding movements in all directions and in any axis or plane.

Such restraint and curtailment of movement is achieved in two ways: In part, by controlling the configuration as well as the length & width dimensions of the aperture space; and in part, by strictly limiting the mil size thickness dimension of the 2$^{nd}$ sheet and intermediate layer within the three-sheet stack construction.

Accordingly, the configuration and axial dimension size or radius of the aperture cavity space should be not less than co-extensive with and preferably be slight greater in size than the true existing overall dimensions and girth of the entire micron-sized photovoltaic cell-integrated chip transponder unit to be deposited within the spatial confines of the aperture cavity volume of the intermediate layer.

It is noted here that the possible Y-axis movement is not of great concern. Of far more concern is that the transponder unit sit "down" in the hole, so that when the badge is placed on a small radius instrument, its marginal edges don't get exposed and therefore avoid being broken by physical impact. For these reasons, a 2$^{nd}$ sheet thickness of about 5-7 mil is considered to be optimal.

Such strict conformity of aperture configuration and axial size/radius will function avoid and eliminate any meaningful freedom of movement for the disposed transponder unit. Then, by carefully choosing an appropriate mil size thickness for the intermediate layer which corresponds closely with the height and girth dimensions of the particular transponder unit—the depth dimension of the aperture space becomes tightly controlled; and all meaningful freedom of movement in the Y-axis direction is diminished for the embedded transponder unit.

Moreover, given that a commercially sold P-Chip® transponder tangibly exists today as either a 500×500×100 micron sized unit or a 250×250×50 micron sized unit—a most preferred mil size and thickness for the intermediate layer is maintained at about 5-6 mils (101.6-127.0 microns) in thickness.

The $3^{rd}$ sheet and transparent top layer—while generally conforming to the length and width dimensions of the other two discrete sheets in the stack construct—should typically be far greater in its thickness or height dimension than the minimal 4 mil size. The reasons for this preference are straight-forward. Even in its minimalist embodiment format, the intended purposes and expected functions of the $3^{rd}$ sheet in the stack construct are three-fold in nature:

First, this top layer and environment exposed stratum is always formed at least in major part of clear and transparent matter in order that light energy signals sent from a remote source be able to pass through its sheet substance without hindrance. It is expected that light energy signals passing through the transparent material substance of this $3^{rd}$ sheet will then encounter the photovoltaic cell of the transponder unit then embedded within the spatial confines of the aperture volume in the $2^{nd}$ sheet and intermediate layer of the stack construct.

Second, this top layer and environmentally exposed sheet serves an effective protective stratum and safety shield for the recognition signal badge as a whole. Such protection and shielding is provided for any recognition signal badge then affixed to a tangible object—in part as protection resistance to impact (compression) forces so that the integrated chip circuitry of the embedded transponder unit remains functional and operational indefinitely; and in part as defensive shielding from the extremely harsh treatments and process conditions caused by repeated sterilization processing, which is obligatory for any surgical instrument or tool.

Third, the top sheet, being transparent for light energy transmission and signal passage, can optimally be markedly extended in its axial length dimension such that this top layer appears as an elongated strip or plank of clear matter whose end portion sections can then be employed for attachment and affixation of the complete recognition signal badge to an exposed surface of a tangible object. Such an axial length-extended uppermost sheet is described in detail subsequently herein as a commercially viable preferred embodiment; and such elements of elongated strip attachment and affixation are there in full.

For all these reasons, it is often highly desirable that the mil thickness dimension of the $3^{rd}$ sheet and outermost layer in the three-tiered composite routinely be 2-5 mils in size; and occasionally be slightly greater in height for some embodiments.

Permitted Variances of Individual Sheet Composition

In general, commercially manufactured and sold adhesive tapes [3M Company] are most preferred for use as the individual layers or strata of material when making the three-sheet stack construct. Such tapes of composed typically of polyethylene, polyvinyl chloride, or polyvinyl compounds. Among these, polyvinyl chemical compositions and blendings are deemed to be the most preferred material substance for all the individual sheets when making the recognition signal badge of the present invention.

Prepared spools, reels, and rolls of preferred polyvinyl compounds and admixed polyvinyl composition tapes can be obtained today from commercial manufacturers (such as 3M Company) in almost any width dimension and mil thickness. Such preferred polyvinyl compound tapes are then cut into any desired length segments for use as individual layers and strata to make the three-sheet stack construct.

The advantages and benefits of using such polyvinyl compound tapes include at least the following:

The tape substance is a non-toxic, biocompatible, and chemically quiescent tape material which resists abrasive scraping, environmental wear and weathering, and chemical degradation.

The tape is available in opaque and dense forms, as well as in clear and transparent light energy transmitting materials.

The tape has a flexible posterior face surface which can be coated with aggressive adhesive compounds which will then allow the tape material to bond with, conform to, and become sealed to smooth, or rough, or even irregular surfaces.

The tape material allows die-cut fashioning into pre-chosen segments of controlled length, width and depth dimensions.

The tape material permits the creation of a micron-sized aperture within a material layer in accordance with a pre-chosen shape, perimeter size and spatial volume—such that a complete transponder unit can be entirely embedded within the limited micron-sized cavity volume of the aperture space, with a tolerance of +/−100 microns.

The tape material allows for the fabrication of a three-sheet stack construct at high manufacturing speeds and at high production capacities using conventionally known tape conversion manufacturing technology—at manufacturing costs commensurate with a retail sales price for the resulting product that the purchasing user can accept.

The tape material offers the inclusion of highly desirable design characteristics—such as an elongated strip configuration which allows the badge to be wound around both the surgical instrument and over itself, while concomitantly still allowing for free and unrestricted passage of light energy signals to activate and energize the photovoltaic chip of the embedded transponder unit.

The tape material offers insulation from electrical current, which can be used with the instrument to cauterize tissue to stop bleeding.

In addition to these characteristics, a range of other desirable properties and features provided by polyvinyl adhesive tapes are listed by Table 2 below.

TABLE 2

| Other Desirable Features & Characteristics Of Polyvinyl/Adhesive Tapes |
| --- |
| Available Tape Mil Thicknesses |
| 0-2 mil |
| 2-3 mil |
| 3-5 mil |
| 5-6 mil |
| 6-7 mil |
| 7+ mil |
| unspecified |
| Tape Temperature Resistance (Duration Over Many Days And Weeks Time) |
| 100° F.-200° F. |
| 200° F.-300° F. |
| 300° F.-400° F. |

TABLE 2-continued

Other Desirable Features & Characteristics
Of Polyvinyl/Adhesive Tapes

400° F.-500° F.
500° F.+
Unspecified

Permitted Variances for Adhesion Bonding and Co-Juncture of Sheets

It is required that each discrete sheet in the three-tier composite be firmly attached and become permanently joined to its adjacent neighbor layer. Adhesive compositions that are heat and moisture resistant, durable, and effect permanent bonding among layers of material are employed for this purpose; and such adhesives are applied to each posterior face surface of each discrete sheet existing in the three-tiered stack construct.

Thus, it is also required that on-demand adherence means be disposed on the posterior face surface (rearward side) of the $1^{st}$ planar sheet and base layer of the three-sheet stack construct such that the entire recognition signal badge will become affixed to the surface of a surgical instrument or tool. Consequently, the adhesive substances employed for the co-juncture of the three sheets together, as well as for subsequent affixation of the recognition signal badge to another object will be chosen in advance to provide particular properties and traits that meet the unique and singular challenges described in detail above.

A representative listing of some suitable adhesives is therefore provided by Table 4 below.

TABLE 4

Range Of Suitable Adhesives*

| Rubber | Standard Acrylic | Modified Acrylic | Silicone |
|---|---|---|---|
| High initial bond | Moderate initial bond | Bonds to wider variety than standard acrylic | Fair initial bond |
| Softer | Firmer | Softer | Very firm |
| Widest variety of surfaces including low surface energy materials* | High surface energy* | Many surfaces | Fewer surfaces |
| Up to 350° F. | Up to 450° F. | Up to 300° F. | Up to 600° F., excellent low temperature performance |
| Fair chemical resistance | Excellent chemical resistance | Good chemical resistance | Excellent chemical resistance |
| Fair UV resistance | Excellent UV resistance | Moderate UV resistance | Excellent UV resistance |
| Poor aging | Excellent aging | Durable | Excellent aging |
| Removable | Permanent | Various | Removable |
| Good solvent resistance | Excellent solvent resistance | Good solvent resistance | Excellent solvent resistance |

*Offered commercially by 3M Company

Permitted Variances in Backing Liner Materials

A wide range of different materials can be selected and employed as a backing liner material. All of these materials will serve as and provide a peel-away sheet barrier from the adhesive(s) disposed upon the posterior face surface of the $1^{st}$ base layer in the commercial formats of the recognition signal badge.

A representative listing of such backing liner materials is set forth by Table 5 below.

TABLE 5

Backing Liner Materials[#]

| Paper | |
|---|---|
| Crepe | Conformable, easy tear. |
| Flatback | Strong, smooth, good for straight line masking. |
| Kraft | Strong, some versions are repulpable. |
| Tissue | Thin, porous to allow adhesive penetration of sheet. |

| Plastic | |
|---|---|
| Polyester | Strong even when thin, chemical resistant, high temperature resistance. |
| Polypropylene | Resistant to most solvents, conformable, tear resistant. |
| Polyethylene | Conformable; easy to stretch; chemical, acid, and moisture resistant, economical. |
| Polyethylene/Polypropylene Co-Polymer | Conformable; chemical, acid, and moisture resistant. |
| UHMW - Polyethylene | High abrasion resistance, low coefficient of friction, antistick surface easy to clean. |
| Polyvinyl Chloride (Vinyl) | Conformable, abrasion resistant, resistant to most chemicals. |
| Polyimide | High temperature resistance, excellent dimensional stability, good insulation properties. |
| Polyamide (Nylon) | High temperature resistance, high strength and toughness, good chemical resistance but can absorb moisture. |
| Polytetrafluoroethylene (PTFE) | Low coefficient of friction, excellent high temperature and chemical resistance, antistick/release properties. |
| Polyvinyl Alcohol (PVA) | Water-soluble, organic solvent resistant, high temperature resistance. |
| Polyurethane | Abrasion and scratch resistant, impact and puncture resistant, UV and corrosion resistant. |
| Polyvinyl Fluoride (e.g., Tedlar ®) | Excellent weather resistance, excellent long-term UV resistance, thin yet stiff feel. |

| Cloth | |
|---|---|
| Cotton | Strong, easy tear by hand, soft and drapable. |
| Glass Cloth | Strong, high temperature resistance, flame-resistant. |
| Polyethylene Coated | Strong yet hand tearable, abrasion resistant, water-resistant, conformable. |

| Non-woven | |
|---|---|
| Fiber | Air permeable, strong enough to hold expanding foams. |

| Metals | |
|---|---|
| Aluminum | Heat and light reflective, moisture and chemical resistant, flame-resistant, outdoor weather resistant, conformable. |
| Lead | Electrically conductive, acid resistant, high conformability, x-ray opacity. |

| Rubber | |
|---|---|
| Neoprene | Abrasion resistant, die-cuttable. |

| Combinations | |
|---|---|
| Paper/Polyethylene | Weather and chemical resistant, hand tearable, stretch resistant. |
| Metalized/Polyester | Reflective, decorative. |
| Glass Cloth/PTFE | High temperature resistance, high strength. |

TABLE 5-continued

Backing Liner Materials[#]

| Glass Cloth/Aluminum | Very high temperature resistance, high strength. |
| Non-woven/Aluminum | High heat and cold resistance. |

[#]Offered commercially by 3M Company

V. Unpredicted Advantages and Unforeseen Benefits of the Recognition Signal Badge (a) The complete recognition signal badge is a millimeter-sized manufactured medallion which contains an embedded photovoltaic cell-activated integrated chip transponder unit; and as such is a discrete and operative article of manufacture which is responsive to a light energy signal sent from any conventional light source.

(b) The complete recognition signal badge is a laminated unit which can be deposited upon and permanently affixed to a very small, exposed surface area of a surgical instrument or tool in a precisely oriented and reliable manner. The complete recognition signal badge becomes firmly joined and affixed to the pre-chosen site and limited area of the tangible, object such that its juncture at that particular place will continue over and endure for at least several calendar years' time.

(c) The complete recognition signal badge is highly resistance to impact (compression) forces and very adequately protects its embedded photovoltaic cell-integrated chip transponder unit such that the electronic circuitry remains functional and operational indefinitely while the surgical instrument or tool is used for its intended purpose. The degree of cushioning and sheath protection offered against the adverse shock effects of impact (compression) forces is sufficiently great that the affixed badge is able to absorb repeated collisions with a hard surface or object; and is consistently able to withstand the major impact shock waves caused by accidentally dropping the badge-affixed surgical instrument on the floor or throwing the surgical tool after use into a disposal bin.

(d) The complete recognition signal badge is a discernible emblem which can be applied to any available exposed surface area on the individual object which is un-intrusive and not directly involved in the intended surgical application or use of that instrument or tool. At this un-intrusive affixation site, the badge not only allows an unobstructed and optically clear travel direction pathway for a transmitted light energy signal to reach the photovoltaic cell in the embedded transponder unit; but also avoids accidental creation of obstructions and unintentional blockage of a clear optical direction of travel and pathway to the embedded transponder.

(e) The complete recognition signal badge is a protected laminate which will repeatedly resist and endure the extremely harsh treatments and process conditions demanded by repeated sterilization processing. It is noted that surgical instrument and tool sterilization is conventionally performed using dry high heat, or via pressurized steam, or by gas exposure, or with gamma light irradiation. Thus it must be appreciated that the photovoltaic cell-activated chip transponder unit embedded within the three-tiered stack structure is thus not only unusually well cushioned and protected; but also adequately shields and safeguards its insulated internal contents from environmental degradation and deterioration caused by repetitious sterilization.

VI. A Highly Preferred Alternative Embodiment and Best Mode Example

A commercially preferred and best mode embodiment of the recognition signal badge is illustrated by FIGS. 15 and 16 respectively. As shown therein, a rectangular-shaped recognition signal badge is shown in overhead and cross-sectional views; and this commercially preferred format ably serves to differentiate and distinguish among different kinds, shapes and sizes of surgical instruments and tools. This rectangular-shaped recognition signal badge contains an internally embedded photovoltaic cell-integrated chip transponder unit which can be encoded with identification data at will; and can generate and will emit a singular identifying RF response signal on-demand; and is easily affixed to a pre-chosen surface and site of only one kind, shape and size of surgical instrument or tool, and whose unique individual characteristics have been correlated with only that one singular identifying RF response signal.

A Preferred Stack Assembly

As shown by FIGS. 15 and 16 respectively, the rectangular-shaped recognition signal badge is a discrete millimeter-sized article of manufacture which is constructed as a protective three-tiered stack assembly 106, and comprises:

(a) A first planar sheet and preformed base layer 110 composed of at least one type of opaque matter which is repellent to water and other aqueous fluids, is resistant to cleaning agents and other noxious chemical compositions, and is enduring of harsh sterilization environments. The preformed base layer 110 in this commercially preferred embodiment has a square-shaped overall configuration; has about a 7 millimeter (mm) sized length and about a 7 mm width; and presents an overall thickness typically ranging from about 3-5 mils.

This first base sheet also presents an anterior face surface 112 as the obverse side and a posterior face surface 114 as the reverse side of the base layer. Both the obverse side 112 and the reverse side 114 of this first sheet 110 have particular functions and application.

(b) A second flat sheet and preformed intermediate layer 120 is composed of at least one type of dense matter which is repellent to water and other aqueous fluids, is resistant to cleaning agents and other noxious chemical compositions, and is enduring of harsh sterilization environments. The preformed second flat sheet 120 presents a discrete anterior face surface 22 as the obverse side and an adhering posterior face surface 124 as the reverse side of the intermediate layer; and the discrete sheet 120 is aligned with, is disposed upon, and is permanently adhered in a fluid-tight manner to the anterior face surface 112 of the first planar sheet 110.

This second flat sheet 120 is a preformed intermediate layer has a fixed configuration and presents millimeter-sized length and width dimensions which are substantially coextensive with the generally square configuration and 7 millimeter sized length and width dimensions of the first planar sheet 110. The illustrated second sheet 20 also has a uniform thickness dimension typically limited to about 5-7 mils.

In addition, the preformed second sheet 120 will always include and invariably present a discernible micron-sized aperture space 126 of fixed shape, perimeter edge and cavity volume. As illustrated by FIGS. 15 and 16, the micron-sized aperture space 126 appears as a round or circular shaped, die-cut opening or hole. However, this circular configuration is merely one of many different shape possibilities; and this rounded spatial format is employed in this illustrated preferred embodiment merely as a convenience.

Nevertheless, without regard to its true configuration in any instance, the dimensions and depth of the aperture space 26 will always be limited in size to be a micron-sized cavity and void volume. Accordingly, the approximate diameter of the illustrated round aperture space 126 will typically range from less than 1,000 microns to about 300 microns; and the depth of the spatial cavity will frequently be only about 5-7 mills in size.

(c) A third rectangularly-shaped sheet 30 and preformed top layer is employed which is composed entirely of a clear material or transparent substance; and which is repellent to water and other aqueous fluids, and is resistant to cleaning agents and other noxious chemical compositions, and is enduring of harsh sterilization environments. The preformed third rectangularly-shaped sheet 130 presents a discrete anterior face surface 132 as the obverse side and an adhering posterior face surface 134 as the reverse side; and is aligned with, is disposed upon, and is permanently adhered in a fluid-tight manner to the anterior face surface 122 of the second flat sheet 120.

In this commercially preferred embodiment, the top sheet 130 will have a rectangularly-shaped configuration; have a length dimension which ranges from 50-200 mm (to allow for 360 degree application to larger circumference instruments); have a width dimension of about 7 mm; and presents a thickness dimension which in this illustrated best mode embodiment is about 3-5 mills in size—but optionally can vary from about 6-15 mills in thickness in alternative embodiments, if and when so desired.

As shown by FIGS. 15 and 16, it is apparent that the length dimension of the transparent top sheet 130 is far greater in size than the length dimensions of both the $1^{st}$ base sheet 110 and the second intermediate sheet 120. Thus, the transparent top sheet 130 has a center portion 133, and two end portions 135 and 137 respectively. The third sheet can be cut to size so that the overall length of the construct is sufficient to wrap at least entirely around the circumference of the surface of the instrument or item to which it is affixed to. The intended uses and value of this organizational format and the two end portions 135 and 137 is described below.

Figure 17:
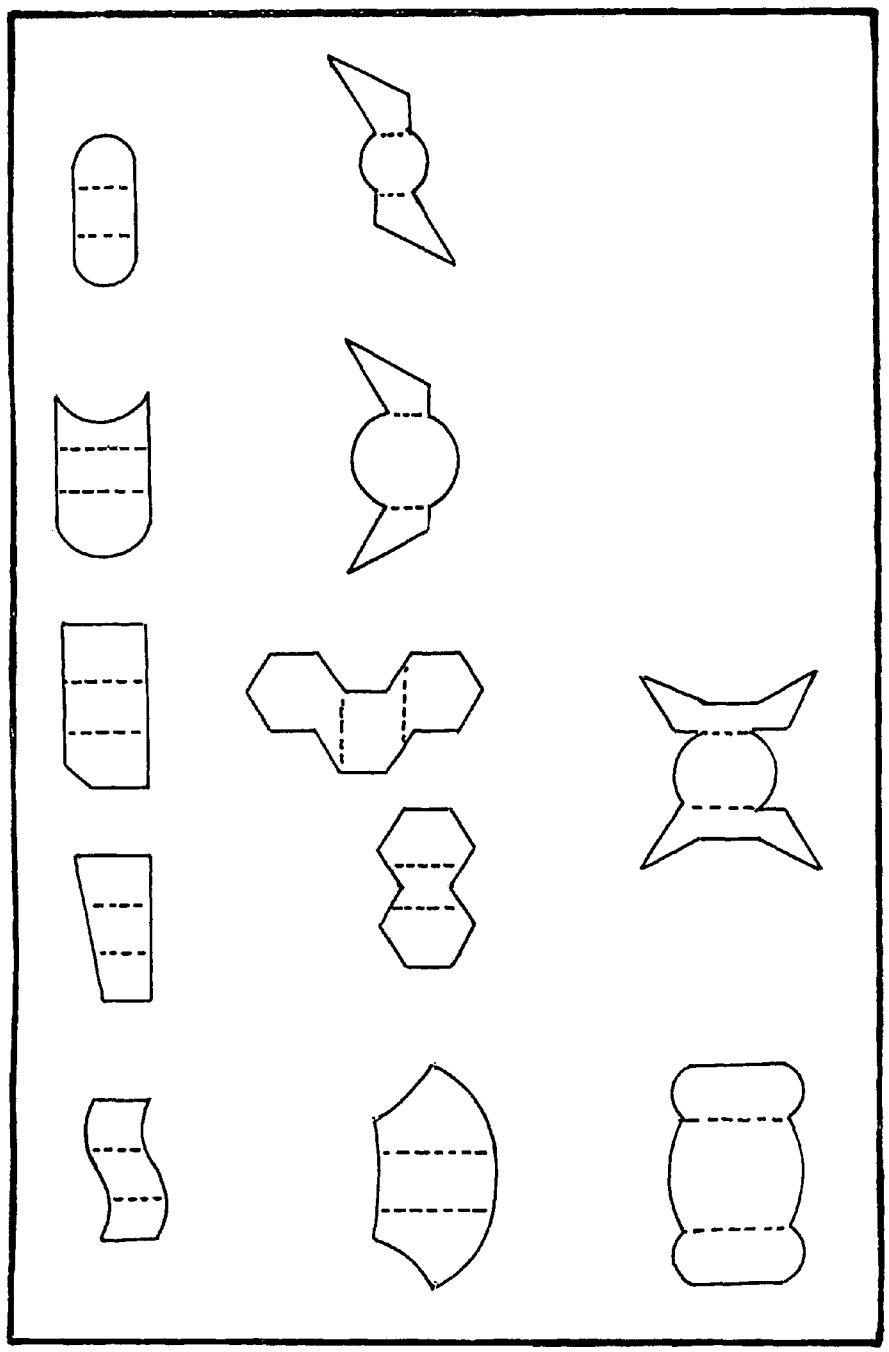
FIG. 17 illustrates the range and variety of alternative shapes and formats for the 3$^{rd}$ sheet of the recognition signal badge shown by FIGS. 15 and 16 respectively.

In addition, it will be appreciated that a number of alternative configurations other than a rectangular shape are available and can be used at will as the $3^{rd}$ sheet 130 and transparent top layer of the three-tiered composite 106. Merely representing the range and variety of this alternative shapes and formats for the $3^{rd}$ sheet 130 are those regular and irregular configurations shown in FIG. 17. Any of the alternative configurations seen in FIG. 17 may be utilized at will in place of the rectangularly-shaped format, as the intended circumstances of usage or one's personal desires dictate.

It is also required that suitable and appropriate affixations means, such as a durable adhesive composition, be disposed as a discrete coating on the posterior face surface (rearward side) of the $1^{st}$ base sheet of the three-sheet stack construct 106. Preferred adhesive compositions are heat and moisture resistant; are durable and long acting; and will effect permanent bonding for and among the individual layers of material. Such adhesives are also typically applied to each posterior face surface of each discrete sheet employed for and existing in the three-tiered stack construct.

Furthermore, in order that the complete rectangularly-shaped badge shown by FIGS. 15 and 16 become properly affixed to only a pre-selected site and surface of a surgical instrument or tool on-demand, a conventional peel-away backing liner 140 is placed upon the adhesive coating then disposed upon the posterior face surface (rearward side) 114 of the $1^{st}$ base sheet 110.

Moreover, for the commercially preferred embodiment, the peel-away backing liner 140 has dimensions that are intentionally co-extensive with those of the $3^{rd}$ top sheet 130. Thus in this illustrated example, the peel-away backing sticker 140 will have a rectangularly-shaped overall configuration; have a length dimension which ranges from about 50-200 mm; and have a width dimension of about 7 mm. However, it is preferred that the peel-away backing liner 140 present a minimal thickness dimension, which in this illustrated embodiment is about 4-6 mills in depth.

In addition, it is intended that a human operator can and will remove this peel-away backing liner 140 by hand before placing the adhesive-coated posterior face surface 114 of the $1^{st}$ base sheet 110 upon a pre-selected site and surface of a surgical instrument or tool.

It is also required that each discrete sheet—i.e., the preformed $1^{st}$ base sheet and the preformed $2^{nd}$ intermediate sheet and the preformed $3^{rd}$ top sheet—forming the three-tier composite become firmly attached and permanently joined in a fluid-tight manner to its adjacent neighbor layer. The fluid-tight juncture and permanent bonding of these three individual sheets together yields a single multi-tier stack construct which is protective and safeguarding against impact forces and collision effects; is repeatedly able to repel water and other aqueous fluids; is highly resistant to cleaning agents and noxious chemical compositions; will provide protection against electrical current flowing through the surface of the object to which the badge is affixed; repetiously will endure and withstand the extremely harsh treatment conditions of repeated sterilization (via any conventionally known method); and will last for a long period of usage extending for at least several years in duration.

The fluid-tight juncture and bonding of these preformed sheets together into a single unified composite arrangement preferably employs high-strength, temperature resistant, and long lasting adhesive substances for this purpose. There are today many different conventionally known and commercially available adhesive compounds and bonding compositions that are heat and moisture resistant, that are high temperature durable, and which can effect permanent bonding of multiple layers. All such adhesives and bonding agents are typically applied as a distinct coating to each posterior face surface of each discrete sheet before joining the individual sheets together for the making of a three-tiered stack construct.

The Embedded Photovoltaic Cell-Integrated Chip Transponder Unit

As shown by FIG. 16 in cross-sectional view, within the commercially preferred three-tiered stack construct 106 resides an operative micron-sized photovoltaic cell-integrated chip transponder unit 150. This transponder unit 150 lies embedded within and is completely contained by the enclosed micron-sized cavity volume of the aperture space 126 within the material substance of the intermediate sheet 120.

The embedded photovoltaic cell-integrated chip transponder unit 150 can be activated on-demand via light energy; and will become energized by light energy signals passing through the transparent sheet 130 of the stack construct 106. After receiving and converting such a light energy transmission, the embedded transponder unit 150 will produce and electronically emit an encoded identification RF response signal—which then travels through the material thickness of the transparent top sheet 130 into the immediately surrounding environment, and can then be detected by a remotely located reader/detector apparatus.

Operationally, each micron-sized photovoltaic cell-integrated chip transponder unit 150 will contain individual encoded information or data which relates to and identifies the object bearing the affixed recognition signal badge. When a remotely located light source sends a light energy signal (e.g., laser light of a pre-chosen frequency and intensity) over a short distance (several meters) to the micron-sized photovoltaic cell-integrated chip transponder unit 150 then embedded within the affixed recognition badge—the photovoltaic cell of the embedded transponder unit will receive and absorb the light energy sent from the remotely located transceiver; and then convert the absorbed light energy into internal electric current power for operating the chip circuitry (which holds coded data indicating the identity of the object to which the recognition badge is attached). The chip circuitry, in turn, then operates to produce and emit a response RF signal(s) corresponding to the transponder's individual coded identity data; and this emitted response RF signal travels over a short distance to a remotely located reader/detector. After the response RF signal(s) is detected and received, the remotely located reader decodes the response RF signal(s) and then typically visually displays the decoded identification information to the surgical technician.

In this commercial embodiment (see FIGS. 15 and 16), the photovoltaic cell—integrated circuit transponder unit embedded in the cavity volume of the aperture space of the second flat sheet is miniscule in scale and size; and is at most about 500 microns square in area, and typically is no more than about 100 microns in thickness or depth. Such micron-sized transponders with photovoltaic cell activated integrated circuitry are today commercially manufactured and sold as the P-Chip® transponder [Pharmaseq Inc., Princeton N.J.]; and the P-Chip® transponder unit is available in at least two different micron-sized constructed versions: A 500×500×100 micron sized unit and a 250×250×50 micron sized unit respectively.

An essential part of the preferred P-Chip® transponder unit is its internal photovoltaic cell, which when illuminated by light energy, is activated and provides adequate electric power for operating the electronic circuits of the chip. The remaining electronic circuitry of the P-Chip® silicon wafer are typically a read-only memory unit for the unique 50-bit ID decoders and counters; and a small simple radio antenna for transmission of a return RF signal.

In addition, a portable RF signal ID reader is also commercially available from the manufacturer [Pharmaseq Inc., Princeton N.J.]; and such an remotely located response-signal ID reader/detector can and will communicate with any personal computer (PC) system via a standard USB port. The Series 8000 PharmaSeq Wand is both suitable and operative for detecting and reading responsive RF signals sent from embedded P-Chip® transponders. This response-signal ID reader/detector is calibrated for object identification applications; and includes CD-ROM with p-Chip Reader Software (compatible with Microsoft Excel, Access, and similar software programs).

Using the Preferred Elongated Strip Embodiment

In order to attach the elongated strip embodiment of the recognition signal badge shown by FIGS. 15 and 16, the backing sticker 140 is peeled by hand away from the adhesive coating on the bottom surface of the three-tiered stack construct 106 (then including an embedded transponder unit); and is affixed to a prechosen site on the surface of a specific instrument or tool. Once the center [i.e., the 5-8 mm×5-8 mm sized $1^{st}$ and 2nd sheets] of the three-tier composite becomes adhered to the chosen site surface, the adhesive coated transparent end portions 135 and 137 of the 3rd sheet 130 will be wound at least one complete turn over the girth of the tangible instrument such that the ends portions 135 and 137 meet and overlap each other around the instrument 1.5 or 2 times. The intentional overlapping of the ends portions 135 and 137 neither obstructs nor hinders free transmission and passage of light energy signals because the material substance of the end portions 135 and 137 is made of transparent or clear matter.

The desired and intended resulting product is a badge-affixed surgical instrument or tool which has become embossed and adorned with an embedded light-activated transponder having an unique number associated with its integrated chip circuitry. After all the surgical instruments needed for any given set or tray are affixed with an individual recognition signal badge, all the badge-affixed instruments are then scanned for accurate identity and then appropriately placed in the surgical set or tray.

Proprietary software will then typically be used to manage all aspects of data relevant to managing or rebuilding the prepared sets or trays (or any other subset of functionality associated with the instruments—including, but not limited to, tracking case usage of the individual instrument (whether or not the instrument was used in surgery), and subsequent tracking of maintenance (i.e., sharpening, tightening, repair, or replacement) for individual instruments based on pre-determined schedules.

A Preferred and Commercially Viable Method for Making an Elongated Recognition Signal Badge The process and series of manipulative steps for making a preferred embodiment and commercially desirable recognition signal badge is illustrated by FIGS. 18A-18K respectively.

Step 1 begins with a backing sticker 140 whose overall dimensions are about 50 mm wide, about 70 mm long, and about 4 mils in thickness. This backing sticker is shown by FIG. 18A.

A $1^{st}$ flat sheet 110 having an adhesive coating 117 disposed upon its posterior face surface 114 as shown by FIG. 18B is then aligned with and joined to the backing sticker 140. The $1^{st}$ planar sheet 110 is an adhesive-backed segment of commercially sold polyvinyl tape (3M Company) which is formed of a durable opaque material; and has overall sheet dimensions which are about 50 mm wide, and about 70 mm long, and about 6 mils in thickness. The juncture of the backing liner 140 and the $1^{st}$ planar sheet 110 together results in the discrete co-joined product 210 shown by FIG. 18C.

Step 2 begins with the making of an elongated $2^{nd}$ flat sheet 120 which contains a series of five individual die-cut apertures 126a-126e which are positioned apart from each other at pre-determined distances. This elongated $2^{nd}$ flat sheet 120 is an adhesive 127 coated segment of commercially sold polyvinyl tape (3M Company) formed of a durable dense material; has overall segment dimensions which are about 10 mm long, 50 mm wide, and about 6 mils in depth; and presents five apertures 26a-26e which are about 600 microns in diameter and 152.4 microns in depth. The elongated $2^{nd}$ flat sheet 120 as an elongated segment is shown by FIG. 18D.

The 6 mil thickness of the intermediate layer of tape with preset multiple die cut apertures is sufficient to provide protection of an embedded micron-sized photovoltaic cell-chip transponder unit in the event of any type of impact force collision; and the 6 mil depth of each discrete apertures 26a-26e provides a cavity volume which is at least as large as the height of the transponder unit to be embedded, which in this instance is 100 microns. The 600 micron diameter and 152.4 micron depth of each aperture space 26a-26e thus provides adequate spatial volume to hold and contain a complete transponder unit which is about 500 microns×500 microns×100 microns in size.

The preformed elongated $2^{nd}$ flat sheet 120 containing a series of five individual die-cut apertures 126a-126e is centrally aligned with and permanently adhered directly to the anterior face surface 112 of the $1^{st}$ planar sheet 110 in the discrete co-joined product 210 (shown by FIG. 18C). This yields the accrued multi-layered sheaf 220 shown by FIG. 18E.

Figure 18F:
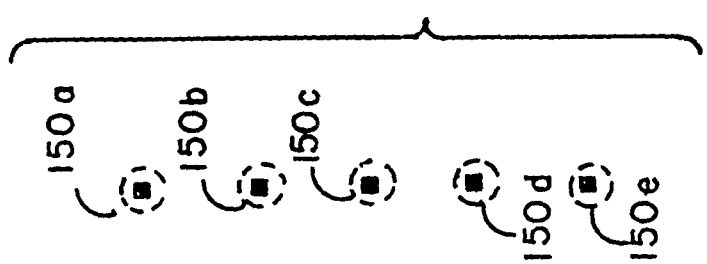

Step 3 begins with the presence of five discrete micron-sized photovoltaic cell-chip transponder units 150a-150e, each presenting overall dimensions which are about 500 microns×500 microns×100 microns in size. The five separate micron-sized photovoltaic cell-chip transponder units 150a-150e are shown by FIG. 18F; and are commercially manufactured and sold as the P-Chip® transponder [Pharmaseq Inc., Princeton N.J.].

One discrete micron-sized photovoltaic cell-chip transponder is then inserted into each of the aperture spaces 26a-26e lying within the accrued multi-layered sheaf 220. The act of transponder unit insertion and its immediate outcome product is the interim workpiece 225 illustrated by FIG. 18G.

Figure 18G:
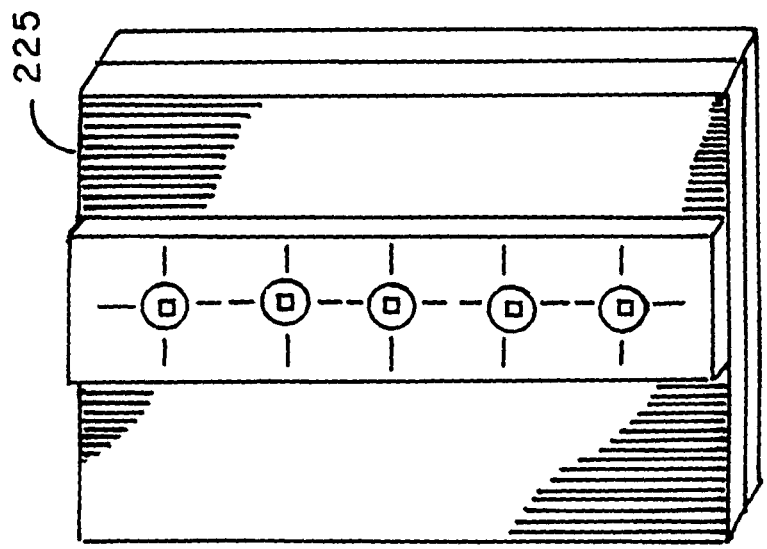

Step 4 begins with the physical alteration of the interim workpiece 225 illustrated by FIG. 18G. By mechanical action, carefully chosen portions of the adhered two layers of polyvinyl tape (i.e., the $2^{nd}$ intermediate sheet 120 and the $1^{st}$ base sheet 110) existing on either side of the aperture-inserted transponder unit are physically removed and stripped away— leaving only the full sized backing sticker 140 and a narrow, centrally positioned, two-layer material mound 190 as the partially-stripped conglomerate 227.

The resulting, centrally positioned, two-layer material mound 190 is a thin and wide mass, approximately 4-5 mm long and 50 mm wide; and substantively includes the five apertures 26a-26e and their previously inserted transponder units 150a-150e (then lying individually within the cavity volume of each aperture space). The effect and result of this physical stripping step and action is the partially-stripped conglomerate 227 shown by FIG. 18H.

Step 5 begins with the making of a $3^{rd}$ level sheet 130 having a durable adhesive coating disposed upon its posterior face surface 134, as shown by FIG. 18I. The $3^{rd}$ level sheet 130 is an adhesive-coated configured segment of commercially sold polyvinyl tape (3M Company) formed of a durable transparent or clear material; and has overall segment dimensions which are about 50 mm wide, and about 70 mm long, and about 6 mils in thickness.

The transparent $3^{rd}$ level sheet 130 with its adhesive coating is then aligned with and directly applied over the centrally positioned two-layer material mound 190 of the partially-stripped conglomerate 227 (shown as FIG. 16H); and then is pressed down along its end sections 135 and 137 and thereby becomes temporarily joined to the exposed side sections 143 and 145 of the co-joined backing sticker 140.

Concomitantly, the adherence and permanent juncture of the center portion 133 of the $3^{rd}$ transparent sheet to the centrally positioned two-layer material mound 190 creates and produces a single three-tier polyvinyl layered assemblage 260 which then also contains five individually embedded micron-sized photovoltaic cell-chip transponders within its material substance, as is shown by FIG. 18J. It will also be noted that the overall dimensions of the unitary three-tier polyvinyl layered assemblage 260 shown by FIG. 18J are about 50 mm in width, and about 70 mm in length, and about 22 mils in thickness.

Step 6 is the last manipulative act in the preferred manufacturing process; and is merely the cutting of the single three-tiered polyvinyl layered assemblage 260 along its 70 mm length dimension into five distinct parts such that five separate, structurally complete, and operative recognition signal badges 300a-300e are formed—each of which is individually 10 mm in width, 70 mm in length, and 18 mils in thickness; and each of which also includes a peel-away backing strip is 10 mm in width, 70 mm in length, and 4 mils in depth. Such a manufactured recognition signal badge 300 is illustrated by FIG. 18K.

The exemplary recognition signal badge 300 of FIG. 18K thus can be affixed on-demand to any exposed site or object surface; and the end sections of the affixed recognition signal badge 300 can be wrapped over and around its central stack section without obscuring or obstructing the free passage of either light energy signals or responsive RF signals.

The present invention is not to be limited in form nor restricted in scope except by the claims appended hereto.

What I claim is:

1. A miniature recognition signal badge suitable for on-demand affixation to and for identifying and sorting among different kinds, shapes and sizes of surgical instruments and tools, said recognition signal badge comprising:

a millimeter-sized three-sheet stack construct which protects against the undesirable effects of impact forces and safeguards its internal contents from degradation by the ambient environment, said millimeter-sized three-sheet stack construct being formed of (α) a preformed $1^{st}$ planar sheet composed of opaque matter,
  wherein said $1^{st}$ planar sheet is repellent to water and other aqueous fluids, is resistant to cleaning agents and other noxious chemical compositions, and is enduring of harsh sterilization environments, and
  wherein said $1^{st}$ planar sheet has a predetermined configuration and millimeter-sized dimensions, and presents an anterior face surface and a posterior face surface, (β) a preformed $2^{nd}$ flat sheet composed of dense matter disposed upon and adhered fluid-tight to said anterior face surface of said $1^{st}$ planar sheet,
  wherein said $2^{nd}$ flat sheet is repellent to water and other aqueous fluids, resistant to cleaning agents and other noxious chemical compositions, and enduring of harsh sterilization environments, and
  wherein said $2^{nd}$ flat sheet presents a pre-chosen configuration and millimeter-sized dimensions which are substantially coextensive with the configuration and dimensions of said $1^{st}$ planar sheet, has an anterior face surface and an adhering posterior face surface, and a includes a closed micron-sized aperture space of fixed shape, perimeter edge and volume, (γ) a preformed $3^{rd}$ level sheet disposed upon and adhered fluid-tight to said anterior face surface of said $2^{nd}$ flat sheet,
  wherein said $3^{rd}$ level sheet is repellent to water and other aqueous fluids, resistant to cleaning agents and other noxious chemical compositions, and enduring of harsh sterilization environments, and
  wherein said $3^{rd}$ level sheet has a pre-chosen configuration and millimeter-sized dimensions not less the dimensions of said $2^{nd}$ flat sheet, and presents an anterior face surface and an posterior face surface, and
  wherein said $3^{rd}$ level sheet is composed at least in part of transparent matter which allows on-demand light energy transmissions and presents at least one discernible light energy transmitting zone which is at least co-extensive in surface area with, is aligned to the perimeter edge of, and encloses the cavity volume of said aperture space in said $2^{nd}$ flat sheet;

an operative micron-sized photovoltaic cell-chip transponder unit embedded within and contained by the closed spatial volume of said aperture in said $2^{nd}$ flat sheet of said three-sheet stack construct, said photovoltaic cell-chip transponder unit becoming activated and energized by light energy to generate and electronically emit an identifying RF response signal into the ambient environment; and an adhesive coating disposed on said posterior face surface of said $1^{st}$ planar sheet of said three-sheet stack construct, said adhesive coating being suitable for on-demand affixation of said three-sheet stack construct and said embedded transponder unit to an exposed surface site of a surgical instrument or tool.

2. The recognition signal badge as recited in claim 1 further comprising a peel-away backing sticker attached to said adhesive coating disposed on said posterior face surface of said $1^{st}$ planar sheet of said three-sheet stack construct.

3. The recognition signal badge as recited in claim 1 wherein said three-sheet stack construct is formed of polyvinyl compositions.

4. The recognition signal badge as recited in claim 1 wherein said three-sheet stack construct varies between 12-25 mills in overall depth.

5. The recognition signal badge as recited in claim 1 wherein said three-sheet stack construct varies between 3-200 millimeters in overall length.

6. The recognition signal badge as recited in claim 1 wherein said three-sheet stack construct varies between 3-12 millimeters in overall width.

7. The recognition signal badge as recited in claim 1 wherein said embedded photovoltaic cell-chip transponder unit is 500 microns×500 microns×100 microns in size.

8. The recognition signal badge as recited in claim 1 wherein said embedded photovoltaic cell-chip transponder unit is 250 microns×250 microns×50 microns in size.

9. An operative recognition system suitable for identifying and sorting among different kinds, shapes and sizes of surgical instruments and tools, said system comprising:

a miniature recognition signal badge suitable for on-demand affixation to a surgical instrument or tool and which is comprised of
a millimeter-sized three-sheet stack construct which protects against the undesirable effects of impact forces and safeguards its internal contents from degradation by the ambient environment, said millimeter-sized three-sheet stack construct being formed of (α) a preformed $1^{st}$ planar sheet composed of opaque matter,
wherein said $1^{st}$ planar sheet is repellent to water and other aqueous fluids, is resistant to cleaning agents and other noxious chemical compositions, and is enduring of harsh sterilization environments, and
wherein said $1^{st}$ planar sheet has a predetermined configuration and millimeter-sized dimensions, and presents an anterior face surface and a posterior face surface, (β) a preformed $2^{nd}$ flat sheet composed of dense matter disposed upon and adhered fluid-tight to said anterior face surface of said $1^{st}$ planar sheet,
wherein said $2^{nd}$ flat sheet is repellent to water and other aqueous fluids, resistant to cleaning agents and other noxious chemical compositions, and enduring of harsh sterilization environments, and
wherein said $2^{nd}$ flat sheet presents a pre-chosen configuration and millimeter-sized dimensions which are substantially coextensive with the configuration and dimensions of said $1^{st}$ planar sheet, has an anterior face surface and an adhering posterior face surface, and a includes a closed micron-sized aperture space of fixed shape, perimeter edge and volume, (γ) a preformed $3^{rd}$ level sheet disposed upon and adhered fluid-tight to said anterior face surface of said $2^{nd}$ flat sheet,
wherein said $3^{rd}$ level sheet is repellent to water and other aqueous fluids, resistant to cleaning agents and other noxious chemical compositions, and enduring of harsh sterilization environments, and
wherein said $3^{rd}$ level sheet has a pre-chosen configuration and millimeter-sized dimensions not less the dimensions of said $2^{nd}$ flat sheet, and presents an anterior face surface and an posterior face surface, and
wherein said $3^{rd}$ level sheet is composed at least in part of transparent matter which allows on-demand light energy transmissions and presents at least one discernible light energy transmitting zone which is at least co-extensive in surface area with, is aligned to the perimeter edge of, and encloses the cavity volume of said aperture space in said $2^{nd}$ flat sheet, an operative micron-sized photovoltaic cell-chip transponder unit embedded within and contained by the closed spatial volume of said aperture in said $2^{nd}$ flat sheet of said three-sheet stack construct, said photovoltaic cell-chip transponder unit becoming activated and energized by light energy to generate and electronically emit an identifying RF response signal into the ambient environment, and an adhesive coating disposed on said posterior face surface of said $1^{st}$ planar sheet of said three-sheet stack construct, said adhesive coating being suitable for on-demand affixation of said three-sheet stack construct and said embedded transponder unit to an exposed surface site of a surgical instrument or tool; and a source of light energy whose light transmissions can be directed to said 3rd sheet of said miniature recognition signal badge; and a RF signal ID reader operative for detecting and reading responsive identifying RF signals sent from said embedded micron-sized photovoltaic cell-chip transponder unit of said miniature recognition signal badge.

10. The operative recognition system as recited in claim 9 wherein said source of light energy transmits laser light of a known frequency and intensity.

11. The operative recognition system as recited in claim 9 wherein said RF signal ID reader detects and reads responsive identifying RF signals of a pre-chosen frequency and amplitude.

* * * * *